(12) United States Patent
Chung et al.

(10) Patent No.: US 8,871,907 B2
(45) Date of Patent: Oct. 28, 2014

(54) GLYCOSYLATED IMMUNOGLOBULIN AND IMMUNOADHESIN COMPRISING THE SAME

(75) Inventors: Yong-Hoon Chung, Seoul (KR); Ki-Wan Yi, Seoul (KR); Hoon-Sik Cho, Seoul (KR); Hong-Gyu Park, Seoul (KR); Kwang-Seong Kim, Hanam-si (KR)

(73) Assignee: Korea Prime Pharm Co., Ltd, Gwangju (KR)

( * ) Notice: Subject to any disclaimer, the term of this patent is extended or adjusted under 35 U.S.C. 154(b) by 1334 days.

(21) Appl. No.: 10/555,538

(22) PCT Filed: May 31, 2005

(86) PCT No.: PCT/KR2005/001627
§ 371 (c)(1),
(2), (4) Date: Nov. 4, 2005

(87) PCT Pub. No.: WO2005/116078
PCT Pub. Date: Dec. 8, 2005

(65) Prior Publication Data
US 2006/0247425 A1 Nov. 2, 2006

(30) Foreign Application Priority Data
May 31, 2004 (KR) .................. 10-2004-0038833

(51) Int. Cl.
C07K 16/00 (2006.01)
C12P 21/08 (2006.01)
A61K 38/17 (2006.01)
C07K 1/00 (2006.01)

(52) U.S. Cl.
CPC ......... *A61K 38/1774* (2013.01); *C07K 2317/21* (2013.01); *C07K 2319/30* (2013.01); *C07K 2317/41* (2013.01); *C07K 2317/526* (2013.01); *C07K 2317/94* (2013.01); *C07K 2317/524* (2013.01)
USPC .................. 530/387.1; 530/387.3; 530/388.1; 530/388.15

(58) Field of Classification Search
None
See application file for complete search history.

(56) References Cited

U.S. PATENT DOCUMENTS

| | | | |
|---|---|---|---|
| 5,447,851 A | 9/1995 | Beutler et al. | |
| 5,521,288 A | 5/1996 | Linsley et al. | |
| 5,844,095 A | 12/1998 | Linsley et al. | |
| 6,046,310 A | 4/2000 | Queen et al. | |
| 6,090,914 A | 7/2000 | Linsley et al. | |
| 6,100,383 A | 8/2000 | Gallatin et al. | |
| 6,225,448 B1 | 5/2001 | Tao et al. | |
| 6,737,056 B1 * | 5/2004 | Presta ........................ | 424/133.1 |
| 6,806,063 B2 * | 10/2004 | Pedersen et al. ............. | 435/69.1 |

FOREIGN PATENT DOCUMENTS

| | | | |
|---|---|---|---|
| KP | 1020040009997 | | 1/2004 |
| WO | WO 2005/070963 | * | 8/2005 |

OTHER PUBLICATIONS

Blast basic local alignment search tool. Apr. 11, 2009. pp. 1-4.*
Lesslaur et al."Recombinant soluble tumor necrosis factor receptor proteins protect mice from lipopolysaccharide-induced lethality"; Eur. J. Immunol. 1991.21: 2883-2886.
Mohler et al, "Soluble tumor nercrosis factor (TNF) receptors are effective therapeutic agents in lethal endotoxemia and function . . . "; Aug. 1, 1993; 151(3): 1548-1561.
Ashkenazi et al "Protection against endotoxic shock by a tumor necrosis factor receptor immunoadhesin" Dec. 1991, PNAS USA vol. 88, pp. 10535-10539.
Peppel et al "A tumor necrosis factor (TNF) receptor-IgG heavy chain chimeric protein as a bivalent antagonist of TNF activity" Dec. 1991 J. Exp. Med. vol. 174, p. 1483-1489.
Scallon et al "Functional comparisions of different tumour necrosis factor receptor/IgG fusion proteins" Nov. 1995 Cytokine, vol. 7, No. 8, pp. 759-770.

* cited by examiner

*Primary Examiner* — Chun Dahle
(74) *Attorney, Agent, or Firm* — Edwards Wildman Palmer LLP; Kongsik Kim; Richard B. Emmons

(57) ABSTRACT

The present invention relates to a glycosylated immunoglobulin or a fragment thereof, in which an immunoglobulin variant, comprising one or more amino acid modifications selected from the group consisting of M160N, A195N, T243N, E265N, Y299T, F331T and Q346N, is additionally glycosylated, and a gene encoding the same. Also, the present invention relates to a glycosylated fusion protein formed as a result of linkage of (a) a glycosylated immunoglobulin or a fragment thereof, in which an immunoglobulin variant having a modified amino acid sequence forming one or more Asn-X-Ser/Thr sequences is additionally glycosylated, with (b) at least one biologically active protein or a portion thereof, a gene encoding the same, a recombination expression vector comprising the gene, a host cell transformed or transfected with the recombinant expression vector, and a method of preparing a glycosylated fusion protein comprising culturing the transformant or transfectant and isolating the glycosylated fusion protein from the culture, and a pharmaceutical composition comprising the glycosylated fusion protein thus prepared.

8 Claims, 4 Drawing Sheets

GLYCOSYLATED IMMUNOGLOBULIN AND IMMUNOADHESIN COMPRISING THE SAME

TECHNICAL FIELD

The present invention relates to a glycosylated immunoglobulin and an immunoadhesin comprising the same. More particularly, the present invention relates to an immunoglobulin or a fragment thereof, which is additionally glycosylated by modification of a specific amino acid residue, and a glycosylated fusion protein formed as a result of linkage of the glycosylated immunoglobulin or a fragment thereof with at least on biologically active protein or a portion thereof.

BACKGROUND ART

Immunoadhesins (or immunoglobulin fusion proteins) are antibody-like molecules resulting from the fusion of a fragment (e.g., Fc portion) of an immunoglobulin and a ligand-binding region of a receptor or an adhesive molecule. The typical immunoadhesins known in the art have the structure of an antibody in which the variable region, participating in antigen recognition, is replaced with a ligand-binding region of a receptor while retaining the Fc portion. For a long time, a large number of patents have described fusion proteins in which a specific region of a physiologically active protein is linked to an antibody (U.S. Pat. Nos. 5,521,288, 5,844,095, 6,046,310, 6,090,914, 6,100,383 and 6,225,448).

The immunoadhesin has the following advantages over a molecule not containing an immunoglobulin:

1) the fusion protein has increased total avidity to a ligand because it has bivalency in a dimer form;

2) the fusion protein is present in an undestroyed form in serum for a longer period of time by virtue of increased molecular stability;

3) effector cells are activated by the Fc (Fragment crystallizable) portion of the immunoglobulin heavy chain; and 4) the fusion protein is isolated and purified by a convenient method, for example, using protein A.

For example, in the case of tumor necrosis factor (hereinafter, referred to simply as "TNF") as a cytokine, to suppress TNF-dependent inflammation responses, tumor necrosis factor receptor (hereinafter, referred to simply as "TNFR") may be used as described in PCT Publication Nos. WO92/16221 and WO95/34326, or a TNFR-immunoglobulin(Ig) fusion protein may be used as described in U.S. Pat. No. 5,447,851 and PCT Publication No. WO94/06476. According to numerous reports, TNFR-Ig fusion proteins have much higher affinity to TNF than the native monomer form or Ig-non-fused form of TNFR (Lesslauer W. et al. Eur. J. Immunol., 1991, vol. 21, p. 2883; Ashkenazi A. et. al. PNAS USA, 1991, vol. 88, p. 10535; Peppel K. et al. J. Exp. Med., 1991, vol. 174, p. 1483; Mohler K. M. et al. J. Immunol. 1993, vol. 151, p. 1548).

With respect to the inhibition of TNF action or the control of immune responses using an Ig fusion protein, a multivalent or multimerized form of the extracellular domain as a functional domain of TNF receptors, CD2 and CTLA4 in an Ig fusion construct is expected to improve the efficacy of the fusion construct. When a monomeric fusion protein (heavy chain fusion protein) of the TNF receptor extracellular domain and the Ig heavy chain is expressed in a cell line simultaneously with another monomeric fusion protein (light chain fusion protein) of the TNF receptor extracellular domain and the Ig light chain, a dimeric fusion protein is produced by the interaction between heavy chain and the light chain. The dimeric fusion protein has two effective domains arranged in parallel like the in vivo form, and has remarkably increased efficacy in comparison with monomeric fusion constructs (Scallon B. J. et al. Cytokine, 1995, vol. 7, p. 759).

However, such an Ig fusion protein in a dimeric form is difficult to industrialize due to the following problems: two genes which are individually fused to the Ig heavy and light chains should be co-introduced into a host cell; when two different fusion proteins are simultaneously expressed in a single cell, their yields greatly decrease; and because all expressed heavy chain fusion proteins and light chain fusion proteins do not participate in the formation of dimers, dimers that fuse a heavy chain fusion protein and a light chain fusion protien are technically difficult to isolate from a mixture with the monomeric heavy chain fusion proteins or light chain fusion proteins.

In this regard, the present inventors constructed a concatameric protein in which a C-terminus of the soluble domain of a biologically active protein is linked to an N-terminus of the soluble domain of an identical or different biologically active protein, using recombinant DNA technology. Also, the present inventors prepared a DNA construct encoding a dimeric protein in which two molecules of a monomeric protein, in which a concatamer of a protein participating in an immune response is linked to the hinge region of an immunoglobulin Fc fragment are disulfide-bonded at the hinge region, and produced a concatamer-linked dimeric fusion protein using recombinant DNA technology based on the DNA construct.

As described above, attempts have been made to improve the efficacy and preparation method of immunoglobulin fusion proteins, but almost all efforts have been unable to increase the stability of the immunoglobulin fusion proteins. In this regard, as disclosed in Korean Pat. Application No. 2002-0045921, the present inventors developed a method of increasing protein stability by adding a glycosylation motif to a conjunction region between a functional domain of a protein and an immunoglobulin Fc region. However, when an immunoadhesin is glycosylated near a functional domain, the protein is not folded correctly or has reduced function.

DISCLOSURE OF THE INVENTION

In this regard, the present inventors constructed a glycosylated fusion protein by introducing an additional glycosylation motif into an immunoglobulin, particularly an Fc portion, of an immunoglobulin fusion protein, and found that the glycosylated fusion protein acts in vivo for a longer period of time than the form not containing a glycosylation motif, thereby leading to the present invention.

Thus, in one aspect, the present invention provides a glycosylated immunoglobulin or a fragment thereof, in which an immunoglobulin variant comprising one or more amino acid modifications selected from the group consisting of M160N, A195N, T243N, E265N, Y299T, F331T and Q346N, is additionally glycosylated.

In another aspect, the present invention provides a DNA encoding a glycosylated immunoglobulin or a fragment thereof, in which an immunoglobulin variant, comprising one or more amino acid modifications selected from the group consisting of M160N, A195N, T243N, E265N, Y299T, F331T and Q346N, is additionally glycosylated.

In a further aspect, the present invention provides a glycosylated fusion protein formed as a result of linkage of (a) a glycosylated immunoglobulin or a fragment thereof, in which an immunoglobulin variant having a modified amino acid sequence forming one or more Asn-X-Ser/Thr sequences is additionally glycosylated, with (b) at least one biologically active protein or a portion thereof.

In yet another aspect, the present invention provides a DNA molecule encoding a glycosylated fusion protein, which is formed as a result of linkage of (a) a glycosylated immunoglobulin or a fragment thereof, in which an immunoglobulin variant having a modified amino acid sequence forming one or more Asn-X-Ser/Thr sequences is additionally glycosylated, with (b) at least one biologically active protein or a portion thereof.

In still another aspect, the present invention provides a recombinant expression vector comprising a DNA molecule encoding a glycosylated fusion protein, which is formed as a result of linkage of (a) a glycosylated immunoglobulin or a fragment thereof, in which an immunoglobulin variant having a modified amino acid sequence forming one or more Asn-X-Ser/Thr sequences is additionally glycosylated, with (b) at least one biologically active protein or a portion thereof.

In still another aspect, the present invention provides a host cell or transfected or transformed with a recombinant expression vector comprising a DNA molecule encoding a glycosylated fusion protein, which is formed as a result of linkage of (a) a glycosylated immunoglobulin or a fragment thereof, in which an immunoglobulin variant having a modified amino acid sequence forming one or more Asn-X-Ser/Thr sequences is additionally glycosylated, with (b) at least one biologically active protein or a portion thereof.

In still aspect, the present invention provides a method of a glycosylated fusion protein, comprising culturing a host cell transfected or transformed with a recombinant expression vector comprising a DNA molecule encoding a glycosylated fusion protein, which is formed as a result of linkage of (a) a glycosylated immunoglobulin or a fragment thereof, in which an immunoglobulin variant having a modified amino acid sequence forming one or more Asn-X-Ser/Thr sequences is additionally glycosylated, with (b) at least one biologically active protein or a portion thereof; and isolating the glycosylated fusion protein from the culture.

In still another aspect, the present invention provides a pharmaceutical composition comprising a glycosylated fusion protein, which is formed as a result of linkage of (a) a glycosylated immunoglobulin or a fragment thereof, in which an immunoglobulin variant having a modified amino acid sequence forming one or more Asn-X-Ser/The sequences is additionally glycosylated, with (b) at least one biologically active protein or a portion thereof.

BRIEF DESCRIPTION OF THE DRAWINGS

The above and other objects features, and other advantages of the present invention will be more clearly understood from the following detailed description taken in conjunction with the accompanying drawings, in which.

BEST MODE FOR CARRYING OUT THE INVENTION

Figure 1:
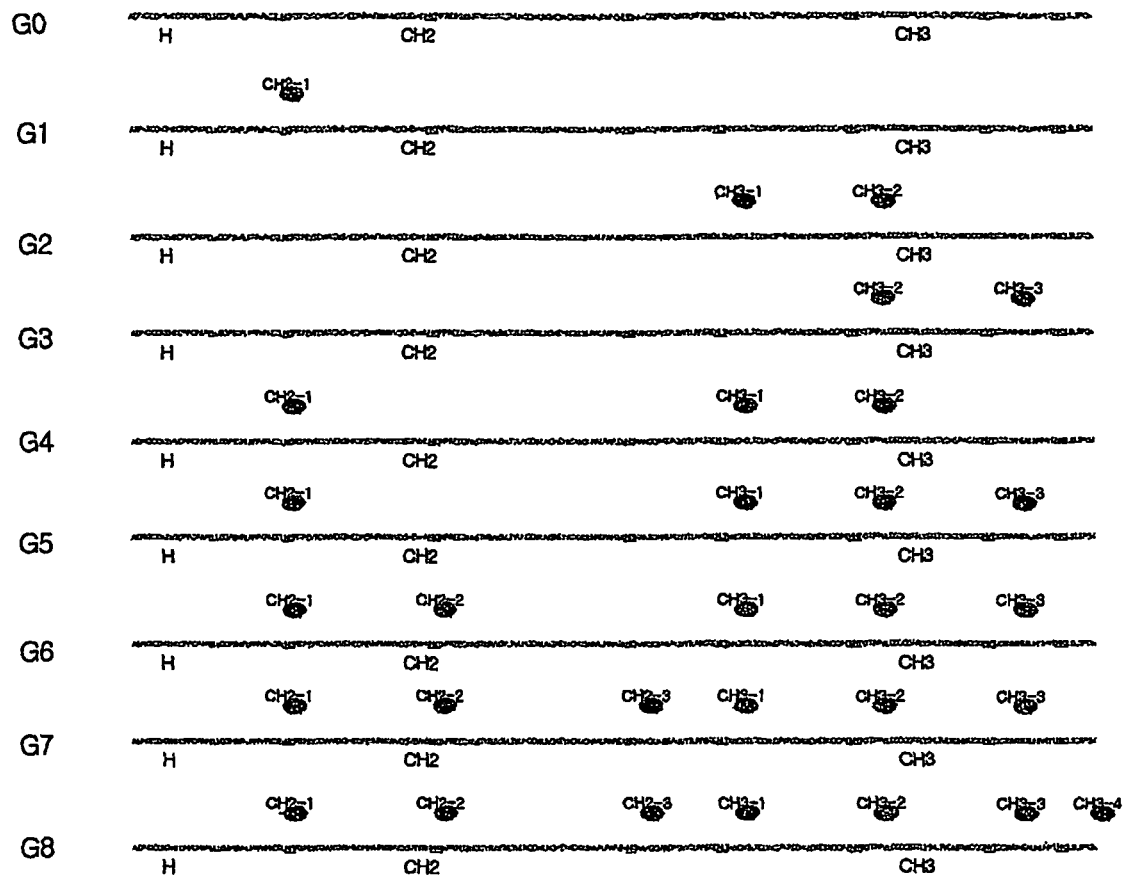
FIG. 1 shows glycosylation on sites of immunoglobulins according to the present invention.

Single capital letters representing amino acids, as used herein, represent the following amino acids according to the standard abbreviations defined by the International Union of Biochemistry:

A: Alanine; B: Asparagine or Asparatic acid;
C: Cysteine; D: Asparatic acid; E: Glutamic acid;
F: Phenylalanine; G: Glycine; H: Histidine;
I: Isoleucine; K: Lysine; L: Leucine; M: Methionine;
N: Asparagine; P: Proline; Q: Glutamine; R: Arginine;
S: Serine; T: Threonine; V: Valine; W: Tryptophan;
Y: Tyrosine; and Z: Glutamine or Glutamic acid.

The designation "(one capital for an amino acid)(amino acid position)(one capital for another amino acid)", as used herein, means that the former amino acid is substituted with the latter amino acid at the designated amino acid position of a given protein. For example, M179N indicates that the methionine residue at the 179th position of a given protein (i.e., IgG) is replaced with asparagine. The amino acid position is numbered from the N-terminus of a mature wild-type protein.

The term "glycosylation" means a process by which proteins produced by eukaryotic cells as host cells are modified by the attachment of sugar chains. The attachment of sugar chains is known to affect properties of proteins as well as in vivo stability and functionality of the proteins. There are two types of glycosylation. O-linked glycosylation links an oligosaccharide chain to a serine and/or threonine residue. N-linked glycosylation links an oligosaccharide chain to an a residue. In particular, N-linked glycosylation occurs in the specific amino acid sequence, Asn-X-Ser/Thr (X is any amino acid excluding proline).

In the present invention, a DNA sequence encoding an immunoglobulin or a fragment thereof is mutated at one or more nucleotides to form an additional glycosylation site at which O-linked or N-linked glycosylation occurs, and the mutated DNA is expressed in a host cell to allow spontaneous glycosylation. In one aspect, a glycosylated immunoglobulin or a fragment thereof according to the present invention is constructed by mutating a DNA sequence encoding an immunoglobulin or a fragment thereof to add and/or increase an Asn-X-Ser/Thr sequence (glycosylation motif) in which N-linked glycosylation occurs.

The "immunoglobulins", which are modified to possess a glycosylation motif in the present invention, are protein molecules that are produced in B cells and serve as antigen receptors specifically recognizing a wide variety of antigens. The molecules have a Y-shaped structure consisting of two identical light chains (L chains) and two identical heavy chains (H chains), in which the four chains are held together by a number of disulfide bonds, including the disulfide bridge between the H chains at the hinge region. The L and H chains comprise variable and constant regions. According to features of the constant regions of H chains, immunoglobulins (Ig) are classified into five isotypes, A (IgA), D (IgD), E (IgE), G (IgG) and M (IgM). The five subtypes possess unique structural an biological properties. These immunoglobulins may all be modified according to the present invention.

Since an immunoadhesin generally contains a fragment of an immunoglobulin, namely, the Fc portion, a glycosylation motif in the present invention is preferably introduced into the Fc portion of an immunoglobulin. The term "Fc portion of an immunoglobulin", as used herein, refers to a fragment having no antigen-binding activity and being easily crystallized, which comprises a hinge region and CH2 and CH3 domains, and a portion responsible for binding of an antibody to effector materials and cells.

In the present invention, a glycosylation motif is preferably created by modifying one or more amino acid residues at positions 160, 195, 243, 265, 299, 331 and 346 of an immunoglobulin (all of these amino acid residues are present at the Fc portion of an immunoglobulin). Thus, in one aspect, the present invention provides a glycosylated immunoglobulin or a fragment thereof, which comprises one or more amino acid modifications selected from the group consisting of M160N, A195N, T243N, E265N, Y299T, F331T and Q346N, and a gene encoding the same. In more detail, a glycosylated immunoglobulin or a fragment thereof listed in Table 1 is provided, which contains combinations of one or more of the aforementioned amino acid modifications.

TABLE 1

Glycosylated immunoglobulins or fragments thereof according to the present invention

| Name | Amino acid modification | SEQ ID NO DNA | SEQ ID NO Protein |
|---|---|---|---|
| Ig-G1 | M160N | 16 | 17 |
| Ig-G2 | E265N; Y299T | 18 | 19 |
| Ig-G3 | Y299T; F331T | 20 | 21 |
| Ig-G4 | M160N; E265N; Y299T | 22 | 23 |
| Ig-G5 | M160N; E265N; Y299T; F331T | 24 | 25 |
| Ig-G6 | M160N; A195N; E265N; Y299T; F331T | 26 | 27 |
| Ig-G7 | M160N; A195N; T243N; E265N; Y299T; F331T | 28 | 29 |
| Ig-G8 | M160N; A195N; T243N; E265N; Y299T; F331T; Q346N | 30 | 31 |

In another aspect, the present invention provides a glycosylated fusion protein formed as a result of linkage of (a) a glycosylated immunoglobulin or a fragment thereof, in which an immunoglobulin variant having a modified amino acid sequence forming one or more Asn-X-Ser/Thr sequences is additionally glycosylated, with (b) at least one biologically active protein or a portion thereof. In a preferred aspect, the fragment of an immunoglobulin includes an Fc portion, and the portion of a biologically active protein includes a soluble extracellular domain.

In one aspect, the glycosylated fusion protein has a monomer structure in which a single polypeptide is formed as a result of linkage of (a) a glycosylated immunoglobulin or a fragment thereof, in which an immunoglobulin having a modified amino acid sequence forming one or more Asn-X-Ser/Thr sequences is additionally glycosylated, with (b) at least one biologically active protein or a portion thereof. The portion of a biologically active protein preferably includes a soluble extracellular domain of the biologically active protein. Two molecules of such a monomeric glycosylated fusion protein may be linked by a disulfide bond at the hinge region to form a dimer structure.

In another aspect, the glycosylated fusion protein has a monomer structure in which a single polypeptide is formed as a result of linkage, in a concatameric form, of (a) a glycosylated immunoglobulin or a fragment of in which an immunoglobulin variant having a modified amino acid sequence forming one or more Asn-X-Ser/Thr sequences is additionally glycosylated, with (b) a first biologically active protein or a portion thereof, and (c) a second biologically active protein or a portion thereof. The first and second biologically active proteins may be identical or different. The portion of a biologically active protein preferably includes a soluble extracellular domain of the biologically active protein. Two molecules of such a monomeric glycosylated fusion protein may be linked by a disulfide bond at the hinge region to form a dimer structure.

In a preferred aspect of the glycosylated fusion protein according to the present invention, the immunoglobulin variant comprises one or more amino acid modifications selected from the group consisting of M160N, A195N, T243N, E265N, Y299T, F331T and Q346N and is glycosylated. In a more preferred aspect, the immunoglobulin variant comprises any one of the amino acid sequences of SEQ ID NO: 16 to SEQ ID NO: 23, and in the most preferred aspect, the amino acid sequence of SEQ ID NO: 19.

The term "biologically active protein", as used herein, refers to a protein, peptide or polypeptide having generally physiological or pharmaceutical activities, which retains a part of its native activities after forming an immunoadhesin. The term "biological activity", as used herein, is not limited in meaning to physiological or pharmaceutical activities. For example, some immunoadhesins, such as those containing an enzyme, can catalyze a reaction in an organic solvent.

Non-limiting examples of the protein, peptide or polypeptide include hemoglobin, serum proteins (e.g., blood factors including factor VII, VIII and factor IX), immunoglobulin, cytokines (e.g., interleukin), α-, β- and γ-interferons, colony-stimulating factors (e.g. G-CSF and GM-CSF), platelet-derived growth factor (PDGF), and phospholipase activating proteins (PLAPs). Other typical biological or therapeutic proteins include insulin, plant proteins (e.g., lectin and ricin), tumor necrosis factor (TNF) and its mutant alleles, growth factors (e.g., issue growth factors and endothelial growth factors such as TGFα or TGFβ), hormones (e.g., follicle-stimulating hormone, thyroid-stimulating hormone, antidiuretic hormone, pigment-concentrating or dispersing hormones and parathyroid hormone, luteinizing hormone-releasing hormone and its derivatives), calcitonin, calcitonin gene related peptide (CGRP), synthetic enkephalin, somatomedin, erythropoietin, hypothalamus releasing factors, prolactin, chronic gonadotropin, tissue plasminogenactivating agents, growth hormone-releasing peptide (GHRP), and thymic humoral factor (THF). Some proteins such as interleukin, interferon or colony-stimulating factor may be produced in a non-glycosylated form by using DNA recombinant techniques. The non-glycosylated proteins may be useful as biologically active materials in the present invention.

In addition, the biologically active materials useful in the present invention include any part of a polypeptide, which has bioactivity in vivo. Examples of the biologically active materials include peptides or polypeptides, fragments of an antibody, single chain-binding proteins (see, U.S. Pat. No. 4,946,778), binding molecules including fusion polypeptides of antibodies or their fragments, polyclonal antibodies, monoclonal antibodies, and catalytic antibodies. Other examples of the biologically active materials include allergen proteins, such as ragweed, antigen E, honeybee venom, or allergen of mites.

In addition, the biologically active material useful in the present invention includes enzymes. Examples of the enzymes include carbohydrate-specific enzymes, proteinase, oxidoreductases, transferase, hydrolases, lyases, isomerases, and ligases. In detail, Non-limiting examples of the enzymes include asparaginase, arginase, arginine deaminase, adenosine deaminase, peroxide dismutase, endotoxinase, catalase, chymotrypsin, lipase, uricase, adenosine dephosphatase, tyrosinase, and bilirubin oxidase. Examples of the carbohydrate-specific enzymes include glucose oxidase, glucodase, galactosidase, glucocerebrosidase, and glucouronidase.

The term "soluble extracellular domain", as used herein, refers to a portion exposed to the extracellular region of an integral membrane protein penetrating the cell membrane comprising phospholipid, wherein the integral membrane protein contains one or more transmembrane domains made up predominantly of hydrophobic amino acids. Such an extracellular domain mainly comprises hydrophilic amino acids, which are typically positioned at the surface of a folded structure of a protein, and thus is soluble in an aqueous environment. Of most cell surface receptor proteins, extracellular domains serve to bind specific ligands, while intracellular domains play an important role in signal transduction.

In one aspect, the glycosylated fusion protein according to the present invention may be prepared by preparing a DNA sequence encoding an immunoglobulin or a fragment thereof which is modified to contain a glycosylation site and linking thereto another DNA sequence encoding a biologically active protein or a portion thereof. In another aspect, the glycosylated fusion protein may be prepared by primarily preparing a DNA sequence (fusion gene) that encodes both an immunoglobulin or a fragment thereof and a biologically active protein or a portion thereof, and mutating the fusion gene to allow the immunoglobulin or the fragment thereof to be glycosylated. The two preparation methods differ from each other only in terms of a DNA sequence serving as a template and are basically identical to preparation methods, known in the art, of a DNA sequence encoding a protein variant. Thus, hereinafter, the present invention intends to focus on a modification method of an immunoglobulin or a fragment thereof into which a glycosylation motif is substantially introduced.

A DNA sequence encoding the glycosylated immunoglobulin or the fragment thereof according to the present invention may be prepared according to various methods known in the art. These methods include, but are not limited to, oligonucleotide-mediated mutagenesis and cassette mutagenesis.

In particular, the DNA sequence encoding the glycosylated immunoglobulin or the fragment thereof according to the present invention is preferably prepared by oligonucleotide-mediated mutagenesis. This technique is well known in the art, and described by Zoller M. et al. (Zoller M. et al. Nuc. Ac. Res. USA, 1982, vol. 10, pp. 6487-6500). In brief, the DNA sequence encoding the glycosylated immunoglobulin or the fragment thereof may be prepared by hybridizing a template DNA (e.g., a plasmid carrying DNA encoding a non-modified or native immunoglobulin or a fragment thereof) with an oligonucleotide coding for a desired modification. After hybridization, a second complete stand complementary to the DNA template may be synthesized by DNA polymerase, and the second may code for the desired modifications.

Typically, oligonucleotides used in the aforementioned methods are composed of about 25 nucleotides. Shorter oligonucleotides can be employed, but optimal oligonucleotides, at both left and right regions of modified codons, contain 12 to 15 nucleotides complementary to a template. These oligonucleotides can effectively hybridize with a template DNA. These oligonucleotides may be synthesized by the techniques known in the art (Crea et al. Proc. Natl. Acad. Sci. USA, 1978, vol. 75, p. 5765).

In one aspects, the present invention provides a DNA sequence encoding an immunoglobulin or a fragment thereof, which carries one amino acid modification (IgG in Table 1). This DNA sequence may be prepared by performing PCR using DNA encoding an immunoglobulin or its fragment as a template and modification synthetic oligonucleotides as primers. Primers hybridize with their complementary single-stranded DNA produced by denaturation of a double-stranded DNA template during heating. DNA polymerase adds nucleotides to the 3'-OH of the modification-encoded primer one by one in a manner complementary to a template in the 5' to 3' direction. The newly synthesized strand incorporates the modification-encoded primer, thus yielding a gene encoding a desired modification. The newly synthesized strand is used as a template DNA in the extension step of PCR, resulting in amplification of a gene encoding the modification.

In another aspect, the present invention provides a DNA sequence encoding an immunoglobulin or a fragment thereof, which carries two or more amino acid modifications. When two or more amino acids to be modified are spaced close to each other on a polypeptide, all desired modifications are encoded in one oligonucleotide and thus simultaneously achieved. Therefore, a mutated immunoglobulin or a fragment thereof having two or more amino acid modifications may be prepared by the same method used to prepare the mutated immunoglobulin or fragment thereof carrying one nucleotide modification, excepting for the use of oligonucleotides containing two or more amino acid modifications as primers.

When two or more amino acids to be modified are spaced far apart (in the case that over 10 amino acids are present between two amino acids to be modified), all desired modifications cannot be encoded in one oligonucleotide. Thus, different methods should be introduced. One method is to prepare individual oligonucleotides for each amino acid modification. When the oligonucleotides are annealed simultaneously to a single-stranded template DNA, a newly synthesized secondary single-stranded DNA encodes all of the desired amino acid modifications. Another approach used in the present invention includes two mutagenesis experiments. In the primary mutagenesis, using natural DNA as a template, one oligonucleotide containing one desired amino acid modification is annealed to the template, and thus heteroduplex DNA is produced. In the secondary mutagenesis, the heteroduplex DNA is used as a template. The template already carries at least one modification. When one oligonucleotide having an additional amino acid modification is annealed to the template, the resulting DNA encodes both of the primary and secondary modifications.

The cassette mutagenesis is also a preferred method for the preparation of DNA encoding the glycosylated immunoglobulin or fragment thereof according to the present invention. This method is based on the technique described by Well J. et al. (Well J. et al. Biochem., 1990, vol. 29, pp. 8509-8517). A starting material is a plasmid (or another vector) containing a gene encoding an immunoglobulin or a fragment thereof to be modified. The cassette mutagenesis is preferably used when a specific restriction enzyme site is present only at a position to be modified. However, this is not essential. If such a restriction enzyme site does not exist, it can be introduced into an appropriate position of a gene encoding an immunoglobulin or a fragment thereof by oligonucleotide-mediated mutagenesis. After a restriction enzyme site is introduced into the plasmid, the plasmid is linearized by treatment with the restriction enzyme. A double-stranded oligonucleotide having a DNA sequence that contains a desired mutation and is located between restriction enzyme sites may be synthesized using a common method. The two strands are individually synthesized and hybridized using a common technique. Such a double-stranded oligonucleotide is typically designated "a cassette". The cassette should be prepared in the form of possessing 3'- and 5'-ends that are compatible with both ends of the linearized plasmid and may be thus directly conjugated to the plasmid. The plasmid comes to contain a DNA encoding a desired glycosylated immunoglobulin or a fragment thereof through the aforementioned procedure.

In addition, the preparation of a DNA sequence encoding a glycosylated immunoglobulin or a fragment thereof according to the present invention may be achieved by a chemical method. In particular, such a DNA sequence may be synthesized by a chemical method using an oligonucleotide synthesizer. An oligonucleotide is made based on an amino acid sequence of an glycosylated immunoglobulin or a fragment thereof, and preferably by selecting a preferable codon using a host cell producing an glycosylated immunoglobulin or a fragment thereof.

With respect to a DNA sequence encoding a glycosylated immunoglobulin or a fragment thereof according to the present invention, the degeneracy in the genetic code, which means that one amino acid is specified by more than one codon, is well known in the art. Thus, there is a plurality of DNA sequences with degeneracy encoding a glycosylated immunoglobulin or a fragment thereof according to the present invention, and they all fall into the scope of the present invention.

Alternatively, the glycosylated fusion protein according to the present invention may be prepared as follows. A DNA sequence encoding the fusion protein (hereinafter, referred to as "fusion gene") is prepared, and is inserted into a vector including one or more expression control sequences regulating the expression of the fusion gene by being operably linked to the fusion gene. Then, a host is transformed or transfected with the resulting recombinant expression vector. The resulting transformant or transfectant is cultured in a suitable medium under conditions suitable for the expression of the fusion gene. A substantially pure glycosylated fusion protein coded by the fusion gene is recovered from the resulting culture.

The term "vector", as used herein, means a DNA molecule that serves as a vehicle capable of stably carrying exogeneous genes into host cells. To be useful in application, a vector should be replicable, have a system for introducing itself into a host cell, and possess selectable markers.

In addition, the term "recombinant expression vector", as used herein, refers to a circular DNA molecule carrying exogeneous genes operably linked thereto to be expressed in a host cell. When introduced into a host cell, the recombinant expression vector has the ability to replicate regardless of host chromosomal DNA at a high copy number and to produce heterogeneous DNA. As generally known in the art, in order to increase the expression level of a transfected gene in a host cell, the gene should be operably linked to transcription and translation regulatory sequences functional in the host cell selected as an expression system. Preferably, the expression regulation sequences and the exogenous genes may be carried in a single expression vector containing selectable markers and a replication origin. In the case that eukaryotic cells are used as an expression system, the expression vector should further comprise expression markers useful in the eukaryotic host cells.

In order to express the DNA sequence (i.e. fusion gene) encoding the glycosylated fusion protein according the present invention, various expression vectors may be employed. Preferably, since an immunoglobulin or a fragment thereof should be glycosylated, expression vectors suitable for eukaryotic host cells should be used. Expression vectors useful for eukaryotic host cells contain expression control sequences derived from, for example, SV40, bovine papilloma virus, adenovirus and cytomegalovirus. In detail, examples of the vectors include pCDNA3.1(+)/Hyg (Invitrogen, Carlsbad, Calif., USA) and pCI-neo (Stratagen, La Jolla, Calif., USA). Expression vectors useful for yeasts include 2µ plasmid and its isoforms, POT1 vector (U.S. Pat. No. 4,931, 373) and pPICZ A, B, or C (Invitrogen). Expression vectors useful for insect cells include pVL 941, pBluebac 4.5 and pMelbac (Invitrogen). However, the present invention is not limited to these examples.

The term "expression cool sequences", as used herein, refers to nucleotide sequences necessary or advantageous for expression of the fusion gene according to the present invention. Each control sequence may be native or foreign to the fusion gene. Non-limiting examples of the expression control sequences include leader sequences, polyadenylation sequences, propeptide sequences, promoters, enhancers or upstream activating sequences, signal peptide sequences, and transcription terminators.

In order to express the fusion gene of the present invention, any of the various expression control sequences may be inserted into the expression vectors used in the present invention. Examples of expression control sequences suitable for directing protein expression in mammalian cells include SV40 and early and late promoters of adenovirus MT-1 (metallothionein gene) promoter, human cytomegalovirus immediate-early gene promoter (CMV), Rouse sarcoma virus (RSV) promoter, and human ubiquitin C (UbC) promoter. In addition, to improve expression levels in mammalian cells, a synthetic intron may be inserted into the 5'-untranslated region of the fusion gene. Examples of expression control sequences suitable for directing protein expression in insect cells include polyhedrin promoter, P10 promoter, baculovirus 39K delayed-early gene promoter and SV40 polyadenylation sequence. Examples of expression control sequences suitable for directing protein expression in yeasts include the promoter of the yeast α-mating system, yeast triose-phosphate isomerase (TPI) promoter and ADH2-4c promoter. Examples of expression control sequences suitable for directing protein expression in fungal cells include ADH3 promoter and terminals.

The term "operably linked" refers to a state in which the fusion gene of the present invention is arranged with such a control sequence in a functional relationship. That is, a gene and control sequences are linked in such a manner that expression of the gene is induced when a suitable molecule (e.g., transcription-activating protein) binds to the control sequence(s). For example, when a pre-sequence or secretory leader facilitates secretion of a mature protein, it is referred to as operably linked to the coding sequence of the protein. A promoter is operably linked with a coding sequence when it regulates transcription of the coding sequence. A ribosome-binding site is operably linked to a coding sequence when it is present at a position allowing translation of the coding sequence. Typically, the term "operably linked" means that linked nucleotide sequences are in contact with each other. In the case of a secretory leader sequence, the term means that it contacts a coding sequence and is present within a reading frame of the coding sequence. However, an enhancer need not necessarily contact a coding sequence. Linkage of the nucleotide sequences may be achieved by ligation at convenient restriction enzyme recognition sites. In the absence of restriction enzyme recognition sites, oligonucleotide adaptors or linkers may be used, which are synthesized by the conventional methods.

On the other hand, host cells having high introduction efficiency of foreign DNA and having high expression levels of an introduced DNA may be used. In particular, as a host cell, a eukaryotic cell capable of glycosylating the fusion protein of the present invention should be used. Examples of suitable yeast host cells include strains of *Saccharomyces* and *Hansenula*. Examples of suitable fungal host cells include *Tricoderma, Fusarium* and *Aspergillus* species. Examples of suitable insect host cells include *Lepidoptora* cell lines such as Sf9 or Sf21. Examples of suitable mammalian host cells include CHO cell lines, COS cell lines such as COS1 or COS7, animal cell lines such as BHK cell line or mouse cells, and tissue-cultured plant cells and human cells.

The fusion gene of the present invention or a recombinant expression vector comprising the same may be introduced into a host cell by the methods described in basic experimental guide books (e.g., Davis et al., Basic Methods in Molecular Biology (1986). The preferred methods for this introduction into a host cell include, for example, calcium phosphate transfection, DEAE-dextran mediated transfection, microinjection, cationic lipid-mediated transfection, electroporation, viral transduction, scrape loading, ballistic introduction, and infection.

In the preparation method of the present invention, the host cells are cultivated in a nutrient medium suitable for production of a polypeptide using methods known in the art. For example, the cells may be cultivated by shake flask cultivation, small-scale or large-scale fermentation in laboratory or industrial fermentors performed in a suitable medium and under conditions allowing the polypeptide to be expressed and/or isolated. The cultivation takes place in a suitable nutrient medium containing carbon and nitrogen sources and inorganic salts, using procedures known in the art. Suitable media are commercially available from commercial suppliers and may be prepared according to published compositions (for example, the catalog of American Type Culture Collection). If the fusion protein is secreted into the nutrient medium, it can be recovered directly from the media. If the fusion protein is not secreted, it can be recovered from cell lysates.

The glycosylated fusion protein of the present invention may be recovered using any one of a number of methods for isolating a polypeptide, which are known in the art. For example, a polypeptide may be recovered from the nutrient medium by conventional procedures including, but not limited to, centrifugation filtration, extraction, spray drying evaporation, or precipitation. Further, the polypeptide may be purified by a variety of procedures known in the art including, but not limited to, chromatography (e.g., ion exchange, affinity, hydrophobicity, and size exclusion), electrophoresis, differential solubility (e.g., ammonium sulfate precipitation), SDS-PAGE, or extraction.

In a further aspect, the present invention provides a pharmaceutical composition comprising the glycosylated fusion protein according to the present invention.

The term "treatment", as used herein, refers to a perfect cure, suppression or alleviation of diseases or disorders. Therefore, the team "therapeutically effective amount", as used herein, means an amount sufficient to achieve the above pharmaceutical effect. In the present invention, the therapeutically effective amount may vary according to the formulation methods, administration modes, patient's age, weight and gender, severity of the illness, diets, administration duration, administration routes, excretion rates, and response sensitivity. Those skilled in the art may readily determine and prescribe a dosage capable of achieving a desired treatment.

In addition, it will be apparent to those skilled in the art that the diseases to be treated by the pharmaceutical composition of the present invention may be varied by varying the type of protein. A glycosylated CTLA4-Ig fusion protein as an embodiment of the present invention is applicable to diseases against which it displays therapeutic effects by inhibiting the action of T-cells, for example, autoimmune diseases such as arthritis or psoriasis, various organ transplants including bone marrow transplants, and varicose veins. Also, fusion proteins with receptors for various cancer-associated cell growth factors may be used in the treatment of cancer because they have improved therapeutic efficacy due to their effects of increasing serum levels of the receptors and blocking angiogenic factors.

The carrier used in the pharmaceutical composition of the present invention includes the commonly used carriers, adjuvants and vehicles, in the pharmaceutical field, which are as a whole called "pharmaceutically acceptable carriers". Non-limiting pharmaceutically acceptable carriers useful in the pharmaceutical composition of the present invention include ion exchange resin, alumina, aluminum stearate, lecithin, serum proteins (e.g., human serum albumin), buffering agents (e.g., sodium phosphate, glycine, sorbic acid, potassium sorbate, partial glyceride mixtures of saturated vegetable fatty acids), water, salts or electrolytes (e.g., protamine sulfate, disodium hydrophosphate, potassium hydrophoshate, sodium chloride, and zinc salts), colloidal silica, magnesium trisilicate, polyvinylpyrrolidone, cellulose-based substrates, polyethylene glycol, sodium carboxymethylcellulose, polyarylate, waxes, polyethylene-polyoxypropylene-block copolymers, polyethylene glycol, and wool fat.

The pharmaceutical composition of the present invention may be administered via any of the common routes, if it is able to reach a desired tissue. Therefore, the pharmaceutical composition of the present invention may be administered topically, parenterally, intraocularly, transdermally, intrarectally and intraluminally, and may be formulated into solutions, suspensions, and the like. The term "parenteral", as used herein, includes subcutaneous, intranasal, intravenous, intraperitoneal, intramuscular, intra-articular, intra-synovial, intrasternal, intracardial, intrathecal, intralesional and intracranial injection or infusion techniques.

In one aspect, the pharmaceutical composition of the preset invention may be formulated as aqueous solutions for parenteral administration. Preferably, a suitable buffer solution, such as Hank's solution, Ringer's solution or physiologically buffered saline, may be employed. Aqueous injection suspensions may be supplemented with substances capable of increasing viscosity of the suspensions, which are exemplified by sodium carboxymethylcellulose, sorbitol and dextran. In addition, suspensions of the active components, such as oily injection suspension, include lipophilic solvents or carriers, which are exemplified by fatty oils such as sesame oil, and synthetic fatty acid esters such as ethyl oleate, triglycerides or liposomes. Polycationic non-lipid amino polymers may also be used as vehicles. Optionally, the suspensions may contain suitable stabilizers or drugs to increase the solubility of components and obtain high concentrations of the components.

The pharmaceutical composition of the present invention is preferably in the form of a sterile injectable preparation, such as a sterile injectable aqueous or oleaginous suspension. Such suspension may be formulated according to the methods known in the art, using suitable dispersing or wetting agents (e.g., Tween 80) and suspending agents. The sterile injectable preparations may also be a sterile injectable solution or suspension in a non-toxic parenterally-acceptable diluent or solvent, such as a solution in 1,3-butanediol. The acceptable vehicles and solvents include mannitol, water, Ringer's solution and isotonic sodium chloride solution. In addition, sterile fixed oils may conventionally be employed as a solvent or suspending medium. For this purpose, any bland fixed oil may be employed, including synthetic mono- or di-glycerides. In addition, fatty acids, such as oleic acid and glyceride derivatives thereof, may be used in the preparation of injectable preparations, like the pharmaceutically acceptable natural oils (e.g., olive oil or castor oil), and particularly, polyoxyethylated derivatives thereof.

The aforementioned aqueous composition is sterilized mainly by filtration using a filter to remove bacteria, mixing with disinfectants or in combination with radiation. The sterilized composition can be hardened, for example, by freeze-drying to obtain a hardened product, and for practical use, the hardened composition is dissolved in sterilized water or a sterilized diluted solution.

In order to increase stability at room temperature, reduce the need for high-cost storage at low temperature, and prolong shelf-life, the pharmaceutical composition of the present invention may be lyophilized. A process for freeze-drying may comprise the steps of freezing, first drying and second drying. After freezing, the composition is heated under pressure to evaporate the water. At the second drying step, residual water is removed from the dry product.

The daily effective dosage of the pharmaceutical composition according to the present invention is typically about 10 µg to about 500 µg per kg body weight, preferably about 20 µg to about 300 µg per kg body weight, and most preferably about 50 µg to about 200 µg per kg body weight. It will be apparent to those skilled in the art that the specific amount of the pharmaceutical composition to be administered to a patient may vary depending on a plurality of factors, including, but not limited to, desired biological activity, the patient's symptoms and drug resistance.

A better understanding of the press invention may be obtained through the following examples. It will be apparent to those skilled in the art that the following examples are provided only to illustrate the present invention, and the scope of the present invention is not limited the examples.

EXAMPLES

TABLE 2

| Information on primers used in the preparation of CTLA4-Ig | | |
|---|---|---|
| Primer Name and others | SEQ ID NO. | Description |
| oligo CTLA4-F-EcoRI | 1 | Containing the 5' end of the soluble extracellular domain of CTLA4 and an EcoRI site |
| oligo CTLA4-R-PstI | 2 | Containing the 3' end of the soluble extracellular domain of CTLA4 and a PstI site |
| oligo IgG1-F-PstI | 3 | Containing the 5' end of the IgG hinge region and a PstI site |
| oligo IgG1-R-XbaI | 4 | Containing the 3' end of IgG and an XbaI site |
| IgG-coding DNA | 5 | DNA encoding wild-type IgG |
| IgG protein | 6 | Wild-type IgG protein |
| CTLA4-IgG-coding DNA | 7 | DNA encoding a fusion protein in which IgG Fc is linked to the soluble extracellular domain of CTLA4 |
| CTLA4-IgG protein | 8 | Fusion protein in which IgG Fc is linked to the soluble exiracellular domain of CTLA4 |

Example 1

A. Preparation of DNA Fragment Encoding Soluble Extracellular Domain of CTLA4

A DNA fragment encoding a soluble extracellular domain of CTLA4 was prepared by PCR using a primer (SEQ ID NO: 1) having a recognition sequence of a restriction enzyme, EcoRI, and a coding sequence for a leader sequence of CTLA4, and another primer (SEQ ID NO: 2) having a PstI recognition sequence and an antisense sequence coding for a 3' end of the soluble extracellular domain of CTLA4. A cDNA template in the PCR was prepared by reverse transcription polymerase chain reaction (RT-PCR) using mRNA extracted from mononuclear cells (T lymphocytes) of healthy adults. mRNA was isolated using a Tri-Reagent mRNA isolation kit (MRC, USA). First $2 \times 10^7$ human T lymphocytes were washed with phosphate buffered saline (PBS, pH 7.2) three times and lysed with 1 ml Tri-Reagent by repetitive pipetting. The cell lysate was mixed with 0.2 ml chloroform by vigorous shaking, allowed to stand at room temperature for 15 min, and centrifuged at 15,000 rpm at 4° C. for 15 min. The supernatant was transferred to a 1.5-ml tube, mixed with 0.5 ml isopropanol, and centrifuged at 15,000 rpm at 4° C. for 15 min. After the supernatant was discarded, the pellet was washed with 1 ml of triple-distilled water (TDW) treated with 75% ethanol- 25% DEPC. The tube was inverted twice or three times and centrifuged at 15,000 rpm at 4° C. for 15 min. After the supernatant was completely removed, the RNA pellet was air-dried to remove remaining ethanol and dissolved in 50 μl DEPC-treated TDW.

B. Preparation of DNA Fragment Encoding Fc Region of IgG1

A DNA fragment encoding an Fc region of IgG1 was prepared by PCR using a primer (SEQ ID NO: 3) having a PstI recognition sequence and a sequence coding for a 5' end of IgG1 Fc, and another primer (SEQ ID NO: 4) having an XbaI recognition sequence and an antisense sequence coding for a 3' end of IgG1 Fc. A cDNA template in the PCR was prepared by RT-PCR using mRNA extracted from peripheral blood cells (B lymphocytes) of patients having a fever of unknown origin, who were in recovery. RT-PCR was carried out using the same reagents under the same conditions as in Example 1, part A.

C. Preparation of Gene Encoding Non-Glycosylated CTLA4-IgG

The DNA fragment encoding the soluble extracellular domain of CTLA4 and the DNA fragment encoding the Fc region of IgG1 were digested with PstI and ligated using T4 DNA ligase. The ligated DNA contained a leader sequence to facilitate protein secretion after expression. The fusion gene fragment thus produced was digested with EcoRI and XbaI and inserted into EcoRI/XbaI sites of pBluescript KS II(+) (Stratagene, USA), which is a commercially available cloning vector. The whole coding region was identified by DNA sequencing (SEQ ID NO: 7). A fusion protein expressed from the fusion gene was designated "CTLA4-IgG", whose predicted amino acid sequence is represented by SEQ ID NO: 8.

Example 2

Preparation of Glycosylated CTLA4-IgG Fusion Proteins

In order to introduce a glycosylation motif into the Fc region of IgG1, seven primers having a nucleotide sequence containing a mutation leading to an amino acid substitution were prepared as follows: in the nucleotide sequence of SEQ ID NO: 5, a 478-480 codon (ATG, Met) was replaced with AAC (Asn, N), a 583-585 codon (GCC, Ala) with AAC (Asn, N), a 727-729 codon (ACC, Thr) with AAC (Asn, N), a 793-795 codon (GAG, Glu) with AAC (Asn, N), a 895-897 codon (TAC, Tyr) with ACC (Thr, T), a 991-993 codon (TTC, Phe) with ACC (Thr, T), and a 1036-1038 codon (CAG, Gln) with AAC (Asn, N). Information on these primers is given in Table 3, below.

TABLE 3

Information on primers used in the preparation of glycosylated CTLA4-Ig

| Primer Name | SEQ ID NO | Description |
| --- | --- | --- |
| mg-hIgG1-CH2-1 | 9 | Primer leading to an N (asparagine) substitution for M (methionine) at position 160 of SEQ ID NO. 6 |
| mg-hIgG1-CH2-2 | 10 | Primer leading to an N (asparagine) substitution for A (alanine) at position 195 of SEQ ID NO. 6 |
| mg-hIgG1-CH2-3 | 11 | Primer leading to an N (asparagine) substitution for T (threonine) at position 243 of SEQ ID NO. 6 |
| mg-hIgG1-CH3-1 | 12 | Primer leading to an N (asparagine) substitution for E (glutamic acid) at position 265 of SEQ ID NO. 6 |
| mg-hIgG1-CH3-2 | 13 | Primer leading to an T (threonine) substitution for Y (tryptophan) at position 299 of SEQ ID NO. 6 |
| mg-hIgG1-CH3-3 | 14 | Primer leading to an T (threonine) substitution for F (phenylalanine) at position 331 of SEQ ID NO. 6 |
| mg-hIgG1-CH3-4 | 15 | Primer leading to an N (asparagine) substitution for Q (glutamine) at position 346 of SEQ ID NO. 6 |

Glycosylated fusion proteins of the present invention were prepared by PCR using the cloning vector carrying CTLA4-hIgG-coding DNA, prepared in Example 1, as a template, and oligonucleotides listed in Table 3 as primers.

In detail, each glycosylated fusion protein was prepared as follows.

(1) CTLA4-hIgG-G1 (G1 variant): one glycosylation motif was created using a primer (SEQ ID NO: 9) designed to have a nucleotide sequence containing a substitution of AAC (Asn, N) for 478-480 nucleotides (ATG, Met) positioned at the Fc region of IgG (SEQ ID NO: 5).

(2) CTLA4-hIgG-G2 (G2 variant): two glycosylation motifs were created using primers (SEQ ID NOS: 12 and 13) designed to have nucleotide sequences containing substitutions of AAC (Asn, N) and ACC (Thr, T) for 793-795 nucleotides (GAG, Glu) and 895-897 nucleotides (TAC, Tyr), respectively, positioned at the Fc region of IgG (SEQ ID NO: 5).

(3) CTLA4-hIgG-G3 (G3 variant): two glycosylation motifs were created using primers (SEQ ID NOS: 13 and 14) designed to have nucleotide sequences containing substitutions of ACC (Thr, T) and ACC (Thr, T) for 895-897 nucleotides (TAC, Tyr) and 991-993 nucleotides (TTC, Phe), respectively, positioned at the Fc region of IgG (SEQ ID NO: 5).

(4) CTLA4-hIgG-G4 (G4 variant): three glycosylation motifs were created using primers (SEQ ID NOS: 9, 12 and 13) designed to have nucleotide sequences containing substitutions of AAC (Asn, N), AAC (Asn, N) and ACC (Thr, T) for 478-480 nucleotides (ATG, Met), 793-795 nucleotides (GAG, Glu) and 895-897 nucleotides (TAC, Tyr), respectively, positioned at the Fc region of IgG (SEQ ID NO: 5).

(5) CTLA4-hIgG-G5 (G5 variant): four glycosylation motifs were created using primers (SEQ ID NOS: 9, 12, 13 and 14) designed to have nucleotide sequences containing substitutions of AAC (Asn, N), AAC (Asn, N), ACC (Thr, T) and ACC (Thr, T) for 478-480 nucleotides (ATG, Met), 793-795 nucleotides (GAG, Glu), 895-897 nucleotides (TAC, Tyr)

and 991-993 nucleotides (TTC, Phe), respectively, positioned at the Fc region of IgG (SEQ ID NO: 5).

(6) CTLA4-hIgG-G6 (G6 variant): five glycosylation motifs were created using primers (SEQ ID NOS: 9, 10, 12, 13 and 14) designed to have nucleotide sequences containing substitutions of AAC (Asn, N), AAC (Asn, N), AAC (Asn, N), ACC (Thr, T) and ACC (Thr, T) for 478-480 nucleotides (ATG, Met), 583-585 nucleotides (GCC, Ala), 793-795 nucleotides (GAG, Glu), 895-897 nucleotides (TAC, Tyr) and 991-993 nucleotides (TTC, Phe), respectively, positioned at the Fc region of IgG (SEQ ID NO: 5).

(7) CTLA4-hIgG-G7 (G7 variant): six glycosylation motifs were created using primers (SEQ ID NOS: 9, 10, 11, 12, 13 and 14) designed to have nucleotide sequences containing substitutions of AAC (Asn, N), AAC (Asn, N), AAC (Asn, N), AAC (Asn, N), ACC (Thr, T) and ACC (Thr, T) for 478-480 nucleotides (ATG, Met), 583-585 nucleotides (GCC, Ala), 727-729 nucleotides (ACC, Thr), 793-795 nucleotides (GAG, Glu), 895-897 nucleotides (TAC, Tyr) and 991-993 nucleotides (TTC, Phe), respectively, positioned at the Fc region of IgG (SEQ ID NO: 5).

(8) CTLA4-hIgG-G8 (G8 variant): seven glycosylation motifs were created using primers (SEQ ID NOS: 9, 10, 11, 12, 13, 14 and 15) designed to have nucleotide sequences containing substitutions of AAC (Asn, N), AAC (Asn, N), AAC (Asn, N), AAC (Asn, N), ACC (Thr, T), ACC (Thr, T) and AAC (Asn, N) for 478-480 nucleotides (ATG, Met), 583-585 nucleotides (GCC, Ala), 727-729 nucleotides (ACC, Thr), 793-795 nucleotides (GAG, Glu), 895-897 nucleotides (TAC, Tyr), 991-993 nucleotides (TTC, Phe) and 1036-1038 nucleotides (CAG, Gln), respectively, positioned at the Fc region of IgG (SEQ ID NO: 5).

The PCR was carried out as follows. To a PCR tube, 1 µl of CTLA4-hIgG DNA (2.2 ng), 1.25 U Pfu DNA polymerase (Stratagene USA), 4U Pfu DNA ligase (Stratagene, USA), 1 µl d of 10× reaction buffer for Pfu DNA ligase, 1 µl of each primer (10 pM), and 2 µl of dNTP (each 10 mM) were added, and triple distilled water was added to a final volume of 20 µl. PCR conditions included two cycles of 3 min at 94° C., 1 min at 61° C. and 1 min at 65° C., and then 29 cycles of 1 min at 94° C., 1 min at 61° C. and 7 min at 65° C., followed by final elongation at 65° C. for 15 min. The PCR products thus obtained were subjected to sequence analysis to determine whether a glycosylation motif was successfully inserted Example 3

A. Expression and Purification of Glycosylated CTLA4-IgG Fusion Proteins

To express glycosylated CTLA4-IgG fusion proteins in Chinese hamster ovary K-1 cells (CHO-K1, ATCC CCL-61, Ovary, Chinese hamster *Cricetulus griseus*), pBluescript KS II(+) plasmid DNA containing a CTLA4-hIgG fusion gene into which a glycosylation motif was inserted was isolated from transformed *E. coli*, and digested with EcoRI and XbaI. The thus-obtained CTLA4-hIgG fusion gene was inserted into EcoRI/XbaI sites of an animal expression vector, pCR™ 3 (Invitrogen, USA). The resulting expression vectors were designated as pCT4Ig-G2 to G8 plasmids. Among them, the pCT4Ig-G2 recombinant expression vector was deposited at the Korean Culture Center of Microorganisms (KCCM) on May 17, 2004 under the provisions of the Budapest Treaty and assigned accession number KCCM 10572.

B. Transfection and Evaluation of Expression of Fusion Genes

Chinese hamster ovary K-1 cells (CHO-K1) were plated onto six-well tissue culture plates (Nunc, USA) at a density of $1$-$3 \times 10^5$ cells per well, and were grown to a 50-80% confluency in 10% FBS-containing DMEM medium. In a serum-free DMEM, 1-2 µg DNA of any one of pCT4Ig-G2 to G8 plasmids was mixed with 2-25 µl of lipofectamine (Gibco BRL, USA), and incubated at room temperature for 15-45 min to form DNA-liposome complexes. Then, the resulting complex was added to the six-well plates. After an incubation period of 5 hrs, the cells were refed with 20% FBS-containing DMEM medium and further cultured for 18-24 hrs. Thereafter, the cells were cultured in 10% FBS-containing DMEM supplemented with 3 mg/ml geneticin (G418, Gibco BRL, USA) for three weeks. Formed colonies were selected and isolated, and then propagated.

Whether or not a fusion gene was expressed was evaluated by ELISA using peroxidase-labeled goat anti-human IgG (KPL, USA). ELISA was carried out as follows. First 1 mg/ml of goat anti-human IgG was diluted to 1:2000 with 0.1 M sodium bicarbonate, and 100 µl of the diluent was aliquotted into a 96-well flexible plate (Falcon, USA). After being sealed with saran wrap, the plate was incubated at 4° C. for over 16 hrs to allow the bottom of the plate to be coated with the antibody. Then, the plate was washed three times with a washing buffer (1×0.1% Tween-20-containing phosphate buffered saline (PBS)), and 100 µl of a dilution buffer (48.5 ml 1×PBS, 1.5 ml FBS, 50 µl Tween-20) was added to each well. 20 µl of a culture supernatant was added to the first well and serially diluted using a micropipette. 0.01 µg/µl of human IgG (Sigma, USA) as a positive control and a culture fluid of non-transfected CHO-K1 cells as a negative control were also diluted like the test sample. After dilutions were completed, the 96-well flexible plate (Falcon, USA) was wrapped with foil, incubated at 37° C. for 1 hr 30 min and washed with the washing buffer three times. Peroxidase-labeled goat anti-human IgG (KPL, USA) was diluted to 1:5000 with the diluent buffer, and 100 µl of the diluent was added to each well, wrapped with foil and incubated at 37° C. for one hour. After the reaction was completed, the plate was developed with a TMB microwell peroxidase substrate system (KPL, USA). Absorbance was measured at 630 nm using a microplate reader (Bio-RAD, Model 550, Japan) to determine whether a fusion gene was expressed and the expression levels of the fusion gene (FIG. 2).

Figure 2:
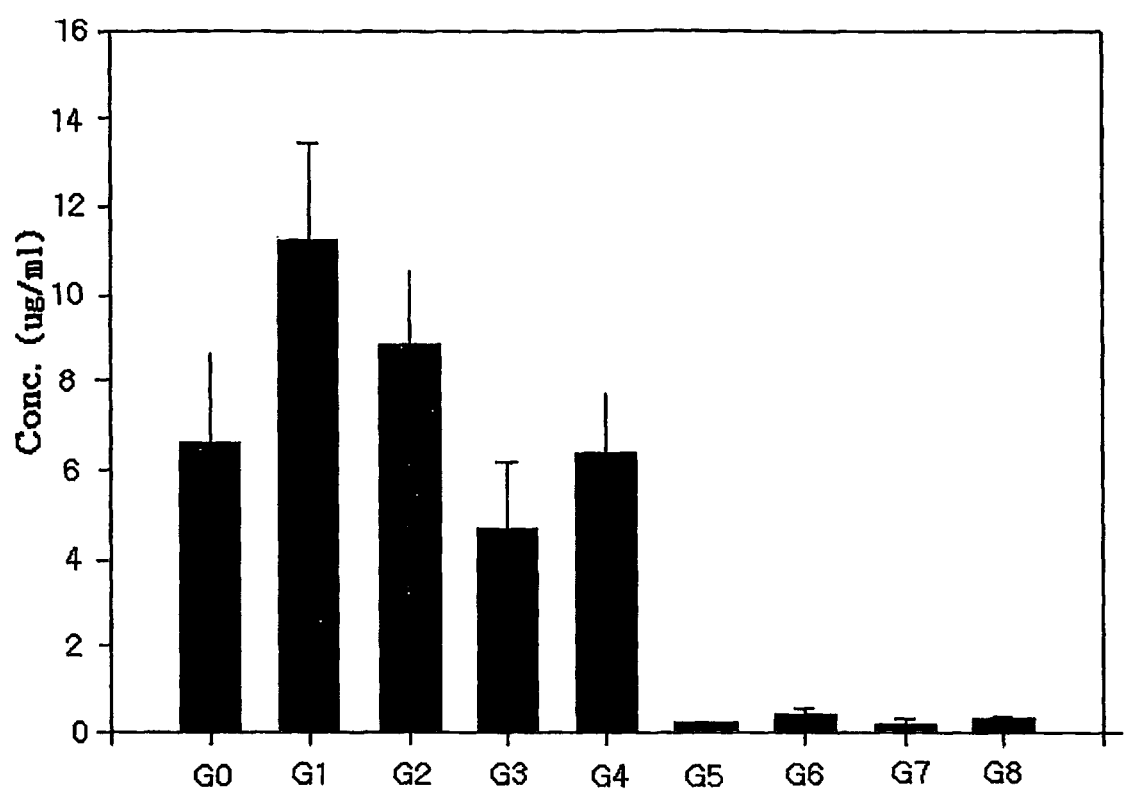
FIG. 2 is a graph showing expression levels of glycosylated CTLA4-IgG fusion proteins according to the present invention.

As shown in FIG. 2, the G1 variant was expressed in the highest levels, followed by G2, G4, G0 and G3 variants. The G5, G6, G7 and G8 variants were found to be rarely expressed.

Example 4

A. Western Blot Analysis

Figure 3:
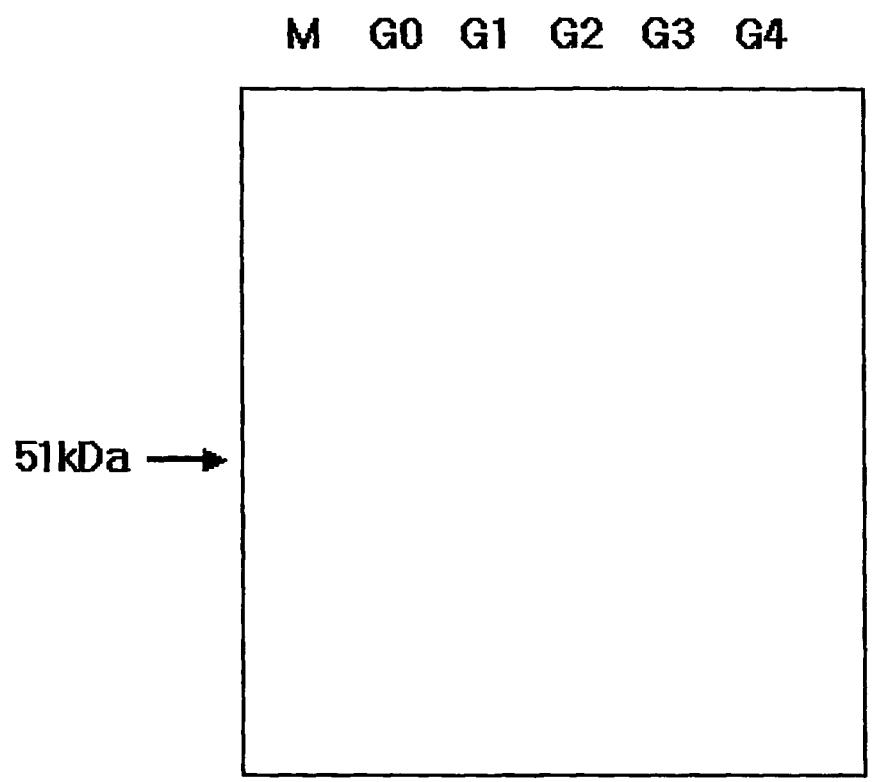
FIG. 3 is a graph showing the results of Western blotting of glycosylated CTLA4-IgG fusion proteins according to the present invention.

An expressed protein was purified by immunoprecipitation and subjected to Western blotting. First 50 µl of protein A-Sepharose beads were placed into a 1.5-ml tube, mixed with 100 µl of buffer A (0.05 M boric acid, 4 M NaCl, pH 9.0), and centrifuged at 13,000 rpm for about 10 sec. After the supernatant was discarded, this step was repeated three times. Each protein sample was mixed with the equilibrated protein A-Sepharose beads and incubated at 4° C. for 3 hrs with rotation to induce binding. Then, the reaction mixture was centrifuged at 13,000 rpm, and the beads were washed with buffer A three times. The beads were mixed with 20 µl of buffer B (0.05 M sodium phosphate, 0.05 M citric acid, 0.3 M NaCl, pH 3.0), and centrifuged at 13,000 rpm to elute bound proteins. The eluted protein sample was mixed with 5× buffer containing 5% β-mercaptoethanol boiled for 5 min, and subjected to reduced SDS-PAGE. A 3.5% Acrylamide gel (0.5 M Tris-HCl (pH 6.8), 0.4% SDS) was used as a stacking gel, and a 10% Acrylamide gel (15 M Tris-HCl (pH 8.8), 0.4% SDS) was used as a running gel. After electrophoresis, proteins were electro-transfrerred onto a 0.4-μm Westran (PVDF transfer membrane, S&S) for 2 hrs at 350 mA. The blot was blocked with 5% skim milk for 1 hr. After being washed with washing buffer (0.1% Tween-20, 1× phosphate buffered saline) three times, the blot was incubated in a 1:2000 dilution of peroxidase-labeled goat anti-human IgG (KPL, USA) for 1 hr. The blot was washed with washing buffer three times, and developed at room temperature for 10 min with 15 ml of a coloring agent, which was made according to a recommended usage method using a DAB substrate kit (VECTOR LABORATORIES, USA). The reaction was terminated with triple-distilled water. The results are given in FIG. 3.

Example 5

Measurement of Serum Half-Lives of Glycosylated CTLA4-hIgG Fusion Proteins in Mice Serum half-lives of glycosylated CTLA4-hIgG fusion proteins were measured in mice as follows. Each fusion protein was intraperitoneally injected into mice (ICR, Samtako Inc., Korea) in a dose of 0.2 mg/kg. Blood samples were collected at given points in time for a minimum of 50 hrs, and protein concentrations were determined according to the same ELISA procedure as in Example 3 (FIG. 4).

Figure 4:
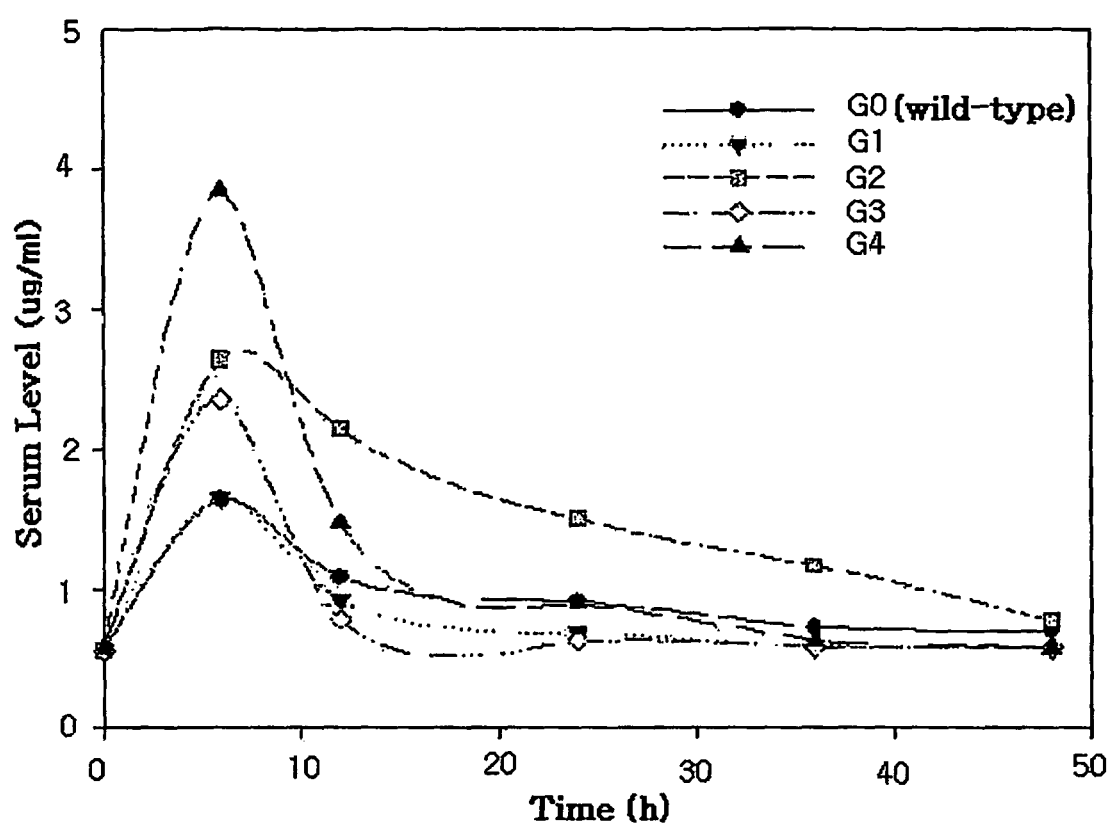
FIG. 4 is a graph showing changes over time in serum levels of glycosylated CTLA4-IgG fusion proteins according to the present invention, in mice intraperitoneally injected with the fusion proteins.

As shown in FIG. 4, the G2, G3 and G4 variants had increased serum levels, whereas the G1 variant displayed reduced blood circulation time compared to the wild type. In particular, the G2 variant exhibited the highest circulation time.

INDUSTRIAL APPLICABILITY

As described hereinbefore, the glycosylated fusion proteins according to the present invention are able to reduce dosage and administration frequency in clinical applications because they have high in vivo stability.

The invention claimed is:

1. A glycosylated immunoglobulin G variant comprising an amino acid sequence selected from the group consisting of the amino acid sequence of SEQ ID NO:19; the amino acid sequence of SEQ ID NO:21; the amino acid sequence of SEQ ID NO:23; the amino acid sequence of SEQ ID NO:25; the amino acid sequence of SEQ ID NO:27; the amino acid sequence of SEQ ID NO:29; and the amino acid sequence of SEQ ID NO:31.

2. The glycosylated immunoglobulin G variant of claim 1, wherein the glycosylated immunoglobulin G variant comprises the amino acid sequence of SEQ ID NO:19.

3. The glycosylated immunoglobulin G variant of claim 1, wherein the glycosylated immunoglobulin G variant comprises the amino acid sequence of SEQ ID NO:21.

4. The glycosylated immunoglobulin G variant of claim 1, wherein the glycosylated immunoglobulin G variant comprises the amino acid sequence of SEQ ID NO:23.

5. The glycosylated immunoglobulin G variant of claim 1, wherein the glycosylated immunoglobulin G variant comprises the amino acid sequence of SEQ ID NO:25.

6. The glycosylated immunoglobulin G variant of claim 1, wherein the glycosylated immunoglobulin G variant comprises the amino acid sequence of SEQ ID NO:27.

7. The glycosylated immunoglobulin G variant of claim 1, wherein the glycosylated immunoglobulin G variant comprises the amino acid sequence of SEQ ID NO:29.

8. The glycosylated immunoglobulin G variant of claim 1, wherein the glycosylated immunoglobulin G variant comprises the amino acid sequence of SEQ ID NO:31.

\* \* \* \* \*

```
                        SEQUENCE LISTING

<160> NUMBER OF SEQ ID NOS: 31

<210> SEQ ID NO 1
<211> LENGTH: 24
<212> TYPE: DNA
<213> ORGANISM: Artificial Sequence
<220> FEATURE:
<223> OTHER INFORMATION: primer, oligo CTLA4-F-EcoRI

<400> SEQUENCE: 1
ccggaattca tgaggacctg gccc                                              24

<210> SEQ ID NO 2
<211> LENGTH: 30
<212> TYPE: DNA
<213> ORGANISM: Artificial Sequence
<220> FEATURE:
<223> OTHER INFORMATION: primer, oligo CTLA4-R-PstI

<400> SEQUENCE: 2
ctctgcagaa tctgggcacg gttcaggatc                                        30

<210> SEQ ID NO 3
<211> LENGTH: 25
<212> TYPE: DNA
<213> ORGANISM: Artificial Sequence
<220> FEATURE:
<223> OTHER INFORMATION: primer, oligo IgG1-F-PstI

<400> SEQUENCE: 3
atctgcagag cccaaatctt gtgac                                             25

<210> SEQ ID NO 4
<211> LENGTH: 34
<212> TYPE: DNA
<213> ORGANISM: Artificial Sequence
<220> FEATURE:
<223> OTHER INFORMATION: primer, oligo IgG1-R-XbaI

<400> SEQUENCE: 4
gctctagagc tcatttaccc ggagacaggg agag                                   34

<210> SEQ ID NO 5
```

<211> LENGTH: 1068
<212> TYPE: DNA
<213> ORGANISM: Homo sapiens
<220> FEATURE:
<221> NAME/KEY: CDS
<222> LOCATION: (1)..(1065)
<223> OTHER INFORMATION: IgG-wild

<400> SEQUENCE: 5

```
cag atc acc ttg aag gag tct ggt ccc acg ctg gtg aaa ccc aca cag      48
Gln Ile Thr Leu Lys Glu Ser Gly Pro Thr Leu Val Lys Pro Thr Gln
  1               5                  10                  15 acc ctc acg ctg acc tgc acg ttc tct gga ttc tca ctc agc aaa agt      96
Thr Leu Thr Leu Thr Cys Thr Phe Ser Gly Phe Ser Leu Ser Lys Ser
             20                  25                  30 gga gtg ggt gtg ggc tgg atc cgt cag ccc cca gga cag gcc ctg gag     144
Gly Val Gly Val Gly Trp Ile Arg Gln Pro Pro Gly Gln Ala Leu Glu
         35                  40                  45 tgg ctt gca ctc att ttt tgg gat gat gat aag cgc tac agc cca tct     192
Trp Leu Ala Leu Ile Phe Trp Asp Asp Asp Lys Arg Tyr Ser Pro Ser
     50                  55                  60 ctg agg acc aga ctc acc atc acc aag gac acc tcc aaa aac cag gtg     240
Leu Arg Thr Arg Leu Thr Ile Thr Lys Asp Thr Ser Lys Asn Gln Val
 65                  70                  75                  80 gtc ctt aca atg acc aac gtg gac cct gcg gac aca gcc aca tat tat     288
Val Leu Thr Met Thr Asn Val Asp Pro Ala Asp Thr Ala Thr Tyr Tyr
                 85                  90                  95 tgt gga tac agt gtt gaa gga tat ggc caa ggt tac cgc ttt cac tcc     336
Cys Gly Tyr Ser Val Glu Gly Tyr Gly Gln Gly Tyr Arg Phe His Ser
            100                 105                 110 tgg ggc cag gga acc ctg gtc acc gtc tgc tca gag ccc aaa tct tgt     384
Trp Gly Gln Gly Thr Leu Val Thr Val Cys Ser Glu Pro Lys Ser Cys
        115                 120                 125 gac aaa act cac aca tgc cca ccg tgc cca gca cct gaa ctc ctg ggg     432
Asp Lys Thr His Thr Cys Pro Pro Cys Pro Ala Pro Glu Leu Leu Gly
    130                 135                 140 gga ccg tca gtc ttc ctc ttc ccc cca aaa ccc aag gac acc ctc atg     480
Gly Pro Ser Val Phe Leu Phe Pro Pro Lys Pro Lys Asp Thr Leu Met
145                 150                 155                 160 atc tcc cgg acc cct gag gtc aca tgc gtg gtg gtg gac gtg agc cac     528
Ile Ser Arg Thr Pro Glu Val Thr Cys Val Val Val Asp Val Ser His
                165                 170                 175 gaa gac cct gag gtc aag ttc aac tgg tac gtg gac ggc gtg gag gtg     576
Glu Asp Pro Glu Val Lys Phe Asn Trp Tyr Val Asp Gly Val Glu Val
            180                 185                 190 cat aat gcc aag aca aag ccg cgg gag gag cag tac aac agc acg tac     624
His Asn Ala Lys Thr Lys Pro Arg Glu Glu Gln Tyr Asn Ser Thr Tyr
        195                 200                 205 cgt gtg gtc agc gtc ctc acc gtc ctg cac cag gac tgg ctg aat ggc     672
Arg Val Val Ser Val Leu Thr Val Leu His Gln Asp Trp Leu Asn Gly
    210                 215                 220 aag gag tac aag tgc aag gtc tcc aac aaa gcc ctc cca gcc ccc atc     720
Lys Glu Tyr Lys Cys Lys Val Ser Asn Lys Ala Leu Pro Ala Pro Ile
225                 230                 235                 240 gag aaa acc atc tcc aaa gcc aaa ggg cag ccc cga gaa cca cag gtg     768
Glu Lys Thr Ile Ser Lys Ala Lys Gly Gln Pro Arg Glu Pro Gln Val
                245                 250                 255 tac acc ctg ccc cca tcc cgg gag gag atg acc aag aac cag gtc agc     816
Tyr Thr Leu Pro Pro Ser Arg Glu Glu Met Thr Lys Asn Gln Val Ser
            260                 265                 270 ctg acc tgc ctg gtc aaa ggc ttc tat ccc agc gac atc gcc gtg gag     864
Leu Thr Cys Leu Val Lys Gly Phe Tyr Pro Ser Asp Ile Ala Val Glu
```

```
Leu Thr Cys Leu Val Lys Gly Phe Tyr Pro Ser Asp Ile Ala Val Glu
            275                 280                 285 tgg gag agc aat ggg cag ccg gag aac aac tac aag acc acg cct ccc      912
Trp Glu Ser Asn Gly Gln Pro Glu Asn Asn Tyr Lys Thr Thr Pro Pro
        290                 295                 300 gtg ctg gac tcc gac ggc tcc ttc ttc ctc tat agc aag ctc acc gtg      960
Val Leu Asp Ser Asp Gly Ser Phe Phe Leu Tyr Ser Lys Leu Thr Val
305                 310                 315                 320 gac aag agc agg tgg cag cag ggg aac gtc ttc tca tgc tcc gtg atg     1008
Asp Lys Ser Arg Trp Gln Gln Gly Asn Val Phe Ser Cys Ser Val Met
                325                 330                 335 cat gag gct ctg cac aac cac tac acg cag aag agc ctc tcc ctg tcc     1056
His Glu Ala Leu His Asn His Tyr Thr Gln Lys Ser Leu Ser Leu Ser
            340                 345                 350 ccg ggt aaa     tga                                                 1068
Pro Gly Lys
        355

<210> SEQ ID NO 6
<211> LENGTH: 355
<212> TYPE: PRT
<213> ORGANISM: Homo sapiens

<400> SEQUENCE: 6

Gln Ile Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Lys Ser
            20                  25                  30

Gly Val Gly Val Gly Trp Ile Arg Gln Pro Pro Gly Gln Ala Leu Glu
        35                  40                  45

Trp Leu Ala Leu Ile Phe Trp Asp Asp Asp Lys Arg Tyr Ser Pro Ser
    50                  55                  60

Leu Arg Thr Arg Leu Thr Ile Thr Lys Asp Thr Ser Lys Asn Gln Val
 65                  70                  75                  80

Val Leu Thr Met Thr Asn Val Asp Pro Ala Asp Thr Ala Thr Tyr Tyr
                85                  90                  95

Cys Gly Tyr Ser Val Glu Gly Tyr Gly Gln Gly Tyr Arg Phe His Ser
            100                 105                 110

Trp Gly Gln Gly Thr Leu Val Thr Val Cys Ser Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255
```

```
Tyr Thr Leu Pro Pro Ser Arg Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Lys
        355

<210> SEQ ID NO 7
<211> LENGTH: 1071
<212> TYPE: DNA
<213> ORGANISM: Homo sapiens
<220> FEATURE:
<221> NAME/KEY: CDS
<222> LOCATION: (1)..(1068)
<223> OTHER INFORMATION: CTLA4-IgG

<400> SEQUENCE: 7 atg cac gtg gcc cag cct gct gtg gta ctg gcc agc agc cga ggc atc      48
Met His Val Ala Gln Pro Ala Val Val Leu Ala Ser Ser Arg Gly Ile
 1               5                  10                  15 gcc agc ttt gtg tgt gag tat gca tct cca ggc aaa gcc act gag gtc      96
Ala Ser Phe Val Cys Glu Tyr Ala Ser Pro Gly Lys Ala Thr Glu Val
                20                  25                  30 cgg gtg aca gtg ctt cgg cag gct gac agc cag gtg act gaa gtc tgt     144
Arg Val Thr Val Leu Arg Gln Ala Asp Ser Gln Val Thr Glu Val Cys
            35                  40                  45 gcg gca acc tac atg atg ggg aat gag ttg acc ttc cta gat gat tcc     192
Ala Ala Thr Tyr Met Met Gly Asn Glu Leu Thr Phe Leu Asp Asp Ser
        50                  55                  60 atc tgc acg ggc acc tcc agt gga aat caa gtg aac ctc act atc caa     240
Ile Cys Thr Gly Thr Ser Ser Gly Asn Gln Val Asn Leu Thr Ile Gln
 65                  70                  75                  80 gga ctg agg gcc atg gac acg gga ctc tac atc tgc aag gtg gag ctc     288
Gly Leu Arg Ala Met Asp Thr Gly Leu Tyr Ile Cys Lys Val Glu Leu
                 85                  90                  95 atg tac cca ccg cca tac tac ctg ggc atg ggc aac gga acc cag att     336
Met Tyr Pro Pro Pro Tyr Tyr Leu Gly Met Gly Asn Gly Thr Gln Ile
                100                 105                 110 tat gta att gat cca gaa ccg tgc cca gat tct gca gag ccc aaa tct     384
Tyr Val Ile Asp Pro Glu Pro Cys Pro Asp Ser Ala Glu Pro Lys Ser
            115                 120                 125 tgt gac aaa act cac aca tgc cca ccg tgc cca gca cct gaa ctc ctg     432
Cys Asp Lys Thr His Thr Cys Pro Pro Cys Pro Ala Pro Glu Leu Leu
        130                 135                 140 ggg gga ccg tca gtc ttc ctc ttc ccc cca aaa ccc aag gac acc ctc     480
Gly Gly Pro Ser Val Phe Leu Phe Pro Pro Lys Pro Lys Asp Thr Leu
145                 150                 155                 160 atg atc tcc cgg acc cct gag gtc aca tgc gtg gtg gtg gac gtg agc     528
Met Ile Ser Arg Thr Pro Glu Val Thr Cys Val Val Val Asp Val Ser
                165                 170                 175 cac gaa gac cct gag gtc aag ttc aac tgg tac gtg gac ggc gtg gag     576
His Glu Asp Pro Glu Val Lys Phe Asn Trp Tyr Val Asp Gly Val Glu
```

```
                    180                 185                 190
gtg cat aat gcc aag aca aag ccg cgg gag gag cag tac aac agc acg     624
Val His Asn Ala Lys Thr Lys Pro Arg Glu Glu Gln Tyr Asn Ser Thr
            195                 200                 205 tac cgt gtg gtc agc gtc ctc acc gtc ctg cac cag gac tgg ctg aat     672
Tyr Arg Val Val Ser Val Leu Thr Val Leu His Gln Asp Trp Leu Asn
210                 215                 220 ggc aag gag tac aag tgc aag gtc tcc aac aaa gcc ctc cca gcc ccc     720
Gly Lys Glu Tyr Lys Cys Lys Val Ser Asn Lys Ala Leu Pro Ala Pro
225                 230                 235                 240 atc gag aaa acc atc tcc aaa gcc aaa ggg cag ccc cga gaa cca cag     768
Ile Glu Lys Thr Ile Ser Lys Ala Lys Gly Gln Pro Arg Glu Pro Gln
            245                 250                 255 gtg tac acc ctg ccc cca tcc cgg gat gag ctg acc aag aac cag gtc     816
Val Tyr Thr Leu Pro Pro Ser Arg Asp Glu Leu Thr Lys Asn Gln Val
        260                 265                 270 agc ctg acc tgc ctg gtc aaa ggc ttc tat ccc agc gac atc gcc gtg     864
Ser Leu Thr Cys Leu Val Lys Gly Phe Tyr Pro Ser Asp Ile Ala Val
    275                 280                 285 gag tgg gag agc aat ggg cag ccg gag aac aac tac aag acc acg cct     912
Glu Trp Glu Ser Asn Gly Gln Pro Glu Asn Asn Tyr Lys Thr Thr Pro
290                 295                 300 ccc gtg ctg gac tcc gac ggc tcc ttc ttc ctc tac agc aag ctc acc     960
Pro Val Leu Asp Ser Asp Gly Ser Phe Phe Leu Tyr Ser Lys Leu Thr
305                 310                 315                 320 gtg gac aag agc agg tgg cag cag ggg aac gtc ttc tca tgc tcc gtg    1008
Val Asp Lys Ser Arg Trp Gln Gln Gly Asn Val Phe Ser Cys Ser Val
            325                 330                 335 atg cat gag gct ctg cac aac cac tac acg cag aag agc ctc tcc ctg    1056
Met His Glu Ala Leu His Asn His Tyr Thr Gln Lys Ser Leu Ser Leu
        340                 345                 350 tcg ccg ggt aaa     tg a                                            1071
Ser Pro Gly Lys
    355

<210> SEQ ID NO 8
<211> LENGTH: 356
<212> TYPE: PRT
<213> ORGANISM: Homo sapiens

<400> SEQUENCE: 8

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Thr Glu Val
             20                  25                  30

Arg Val Thr Val Leu Arg Gln Ala Asp Ser Gln Val Thr Glu Val Cys
         35                  40                  45

Ala Ala Thr Tyr Met Met Gly Asn Glu Leu Thr Phe Leu Asp Asp Ser
     50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Met Gly Asn Gly Thr Gln Ile
            100                 105                 110

Tyr Val Ile Asp Pro Glu Pro Cys Pro Asp Ser Ala Glu Pro Lys Ser
        115                 120                 125

Cys Asp Lys Thr His Thr Cys Pro Pro Cys Pro Ala Pro Glu Leu Leu
```

```
                130                 135                 140
Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355

<210> SEQ ID NO 9
<211> LENGTH: 26
<212> TYPE: DNA
<213> ORGANISM: Artificial Sequence
<220> FEATURE:
<223> OTHER INFORMATION: primer, mg-hIgG1-CH2-1

<400> SEQUENCE: 9
tccgggagat gttgagggtg tccttg                                        26

<210> SEQ ID NO 10
<211> LENGTH: 25
<212> TYPE: DNA
<213> ORGANISM: Artificial Sequence
<220> FEATURE:
<223> OTHER INFORMATION: primer, mg-hIgG1-CH2-2

<400> SEQUENCE: 10
gctttgtctt gttattatgc acctc                                         25

<210> SEQ ID NO 11
<211> LENGTH: 25
<212> TYPE: DNA
<213> ORGANISM: Artificial Sequence
<220> FEATURE:
<223> OTHER INFORMATION: primer, mg-hIgG1-CH2-3

<400> SEQUENCE: 11
ctttggagat gttttctcg atggg                                          25
```

<210> SEQ ID NO 12
<211> LENGTH: 25
<212> TYPE: DNA
<213> ORGANISM: Artificial Sequence
<220> FEATURE:
<223> OTHER INFORMATION: primer, mg-hIgG1-CH3-1

<400> SEQUENCE: 12
tcttggtcag gttatcccgg gatgg                                   25

<210> SEQ ID NO 13
<211> LENGTH: 25
<212> TYPE: DNA
<213> ORGANISM: Artificial Sequence
<220> FEATURE:
<223> OTHER INFORMATION: primer, mg-hIgG1-CH3-2

<400> SEQUENCE: 13
gcgtggtctt ggtgttgttc tccgg                                   25

<210> SEQ ID NO 14
<211> LENGTH: 25
<212> TYPE: DNA
<213> ORGANISM: Artificial Sequence
<220> FEATURE:
<223> OTHER INFORMATION: primer, mg-hIgG1-CH3-3

<400> SEQUENCE: 14
cggagcatga ggtgacgttc ccctg                                   25

<210> SEQ ID NO 15
<211> LENGTH: 26
<212> TYPE: DNA
<213> ORGANISM: Artificial Sequence
<220> FEATURE:
<223> OTHER INFORMATION: primer, mg-hIgG1-CH3-4

<400> SEQUENCE: 15
agaggctctt gttcgtgtag tggttg                                  26

<210> SEQ ID NO 16
<211> LENGTH: 1068
<212> TYPE: DNA
<213> ORGANISM: Homo sapiens
<220> FEATURE:
<221> NAME/KEY: CDS
<222> LOCATION: (1)..(1065)
<223> OTHER INFORMATION: Ig-G1

<400> SEQUENCE: 16

```
cag atc acc ttg aag gag tct ggt ccc acg ctg gtg aaa ccc aca cag      48
Gln Ile Thr Leu Lys Glu Ser Gly Pro Thr Leu Val Lys Pro Thr Gln
 1               5                  10                  15 acc ctc acg ctg acc tgc acg ttc tct gga ttc tca ctc agc aaa agt      96
Thr Leu Thr Leu Thr Cys Thr Phe Ser Gly Phe Ser Leu Ser Lys Ser
             20                  25                  30 gga gtg ggt gtg ggc tgg atc cgt cag ccc cca gga cag gcc ctg gag     144
Gly Val Gly Val Gly Trp Ile Arg Gln Pro Pro Gly Gln Ala Leu Glu
         35                  40                  45 tgg ctt gca ctc att ttt tgg gat gat gat aag cgc tac agc cca tct     192
Trp Leu Ala Leu Ile Phe Trp Asp Asp Asp Lys Arg Tyr Ser Pro Ser
     50                  55                  60 ctg agg acc aga ctc acc atc acc aag gac acc tcc aaa aac cag gtg     240
Leu Arg Thr Arg Leu Thr Ile Thr Lys Asp Thr Ser Lys Asn Gln Val
 65                  70                  75                  80
```

```
          65                  70                  75                  80
gtc ctt aca atg acc aac gtg gac cct gcg gac aca gcc aca tat tat    288
Val Leu Thr Met Thr Asn Val Asp Pro Ala Asp Thr Ala Thr Tyr Tyr
                 85                  90                  95 tgt gga tac agt gtt gaa gga tat ggc caa ggt tac cgc ttt cac tcc    336
Cys Gly Tyr Ser Val Glu Gly Tyr Gly Gln Gly Tyr Arg Phe His Ser
            100                 105                 110 tgg ggc cag gga acc ctg gtc acc gtc tgc tca gag ccc aaa tct tgt    384
Trp Gly Gln Gly Thr Leu Val Thr Val Cys Ser Glu Pro Lys Ser Cys
        115                 120                 125 gac aaa act cac aca tgc cca ccg tgc cca gca cct gaa ctc ctg ggg    432
Asp Lys Thr His Thr Cys Pro Pro Cys Pro Ala Pro Glu Leu Leu Gly
    130                 135                 140 gga ccg tca gtc ttc ctc ttc ccc cca aaa ccc aag gac acc ctc aac    480
Gly Pro Ser Val Phe Leu Phe Pro Pro Lys Pro Lys Asp Thr Leu Asn
145                 150                 155                 160 atc tcc cgg acc cct gag gtc aca tgc gtg gtg gtg gac gtg agc cac    528
Ile Ser Arg Thr Pro Glu Val Thr Cys Val Val Val Asp Val Ser His
                165                 170                 175 gaa gac cct gag gtc aag ttc aac tgg tac gtg gac ggc gtg gag gtg    576
Glu Asp Pro Glu Val Lys Phe Asn Trp Tyr Val Asp Gly Val Glu Val
            180                 185                 190 cat aat gcc aag aca aag ccg cgg gag gag cag tac aac agc acg tac    624
His Asn Ala Lys Thr Lys Pro Arg Glu Glu Gln Tyr Asn Ser Thr Tyr
        195                 200                 205 cgt gtg gtc agc gtc ctc acc gtc ctg cac cag gac tgg ctg aat ggc    672
Arg Val Val Ser Val Leu Thr Val Leu His Gln Asp Trp Leu Asn Gly
    210                 215                 220 aag gag tac aag tgc aag gtc tcc aac aaa gcc ctc cca gcc ccc atc    720
Lys Glu Tyr Lys Cys Lys Val Ser Asn Lys Ala Leu Pro Ala Pro Ile
225                 230                 235                 240 gag aaa acc atc tcc aaa gcc aaa ggg cag ccc cga gaa cca cag gtg    768
Glu Lys Thr Ile Ser Lys Ala Lys Gly Gln Pro Arg Glu Pro Gln Val
                245                 250                 255 tac acc ctg ccc cca tcc cgg gat gag ctg acc aag aac cag gtc agc    816
Tyr Thr Leu Pro Pro Ser Arg Asp Glu Leu Thr Lys Asn Gln Val Ser
            260                 265                 270 ctg acc tgc ctg gtc aaa ggc ttc tat ccc agc gac atc gcc gtg gag    864
Leu Thr Cys Leu Val Lys Gly Phe Tyr Pro Ser Asp Ile Ala Val Glu
        275                 280                 285 tgg gag agc aat ggg cag ccg gag aac aac tac aag acc acg cct ccc    912
Trp Glu Ser Asn Gly Gln Pro Glu Asn Asn Tyr Lys Thr Thr Pro Pro
    290                 295                 300 gtg ctg gac tcc gac ggc tcc ttc ttc ctc tat agc aag ctc acc gtg    960
Val Leu Asp Ser Asp Gly Ser Phe Phe Leu Tyr Ser Lys Leu Thr Val
305                 310                 315                 320 gac aag agc agg tgg cag cag ggg aac gtc ttc tca tgc tcc gtg atg   1008
Asp Lys Ser Arg Trp Gln Gln Gly Asn Val Phe Ser Cys Ser Val Met
                325                 330                 335 cat gag gct ctg cac aac cac tac acg cag aag agc ctc tcc ctg tcc   1056
His Glu Ala Leu His Asn His Tyr Thr Gln Lys Ser Leu Ser Leu Ser
            340                 345                 350 ccg ggt aaa     tga                                               1068
Pro Gly Lys
        355

<210> SEQ ID NO 17
<211> LENGTH: 355
<212> TYPE: PRT
<213> ORGANISM: Homo sapiens
```

-continued

<400> SEQUENCE: 17

```
Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Lys Ser
             20                  25                  30

Gly Val Gly Val Gly Trp Ile Arg Gln Pro Pro Gly Gln Ala Leu Glu
         35                  40                  45

Trp Leu Ala Leu Ile Phe Trp Asp Asp Lys Arg Tyr Ser Pro Ser
     50                  55                  60

Leu Arg Thr Arg Leu Thr Ile Thr Lys Asp Thr Ser Lys Asn Gln Val
 65                  70                  75                  80

Val Leu Thr Met Thr Asn Val Asp Pro Ala Asp Thr Ala Thr Tyr Tyr
                 85                  90                  95

Cys Gly Tyr Ser Val Glu Gly Tyr Gly Gln Gly Tyr Arg Phe His Ser
                100                 105                 110

Trp Gly Gln Gly Thr Leu Val Thr Val Cys Ser Glu Pro Lys Ser Cys
            115                 120                 125

Asp Lys Thr His Thr Cys Pro Pro Cys Pro Ala Pro Glu Leu Leu Gly
        130                 135                 140

Gly Pro Ser Val Phe Leu Phe Pro Pro Lys Pro Lys Asp Thr Leu Asn
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Lys
        355
```

<210> SEQ ID NO 18
<211> LENGTH: 1068
<212> TYPE: DNA
<213> ORGANISM: Homo sapiens
<220> FEATURE:
<221> NAME/KEY: CDS
<222> LOCATION: (1)..(1065)
<223> OTHER INFORMATION: Ig-G2

<400> SEQUENCE: 18

```
cag atc acc ttg aag gag tct ggt ccc acg ctg gtg aaa ccc aca cag      48
Gln Ile Thr Leu Lys Glu Ser Gly Pro Thr Leu Val Lys Pro Thr Gln
  1               5                  10                  15 acc ctc acg ctg acc tgc acg ttc tct gga ttc tca ctc agc aaa agt      96
Thr Leu Thr Leu Thr Cys Thr Phe Ser Gly Phe Ser Leu Ser Lys Ser
             20                  25                  30 gga gtg ggt gtg ggc tgg atc cgt cag ccc cca gga cag gcc ctg gag     144
Gly Val Gly Val Gly Trp Ile Arg Gln Pro Pro Gly Gln Ala Leu Glu
         35                  40                  45 tgg ctt gca ctc att ttt tgg gat gat gat aag cgc tac agc cca tct     192
Trp Leu Ala Leu Ile Phe Trp Asp Asp Asp Lys Arg Tyr Ser Pro Ser
     50                  55                  60 ctg agg acc aga ctc acc atc acc aag gac acc tcc aaa aac cag gtg     240
Leu Arg Thr Arg Leu Thr Ile Thr Lys Asp Thr Ser Lys Asn Gln Val
 65                  70                  75                  80 gtc ctt aca atg acc aac gtg gac cct gcg gac aca gcc aca tat tat     288
Val Leu Thr Met Thr Asn Val Asp Pro Ala Asp Thr Ala Thr Tyr Tyr
                 85                  90                  95 tgt gga tac agt gtt gaa gga tat ggc caa ggt tac cgc ttt cac tcc     336
Cys Gly Tyr Ser Val Glu Gly Tyr Gly Gln Gly Tyr Arg Phe His Ser
            100                 105                 110 tgg ggc cag gga acc ctg gtc acc gtc tgc tca gag ccc aaa tct tgt     384
Trp Gly Gln Gly Thr Leu Val Thr Val Cys Ser Glu Pro Lys Ser Cys
        115                 120                 125 gac aaa act cac aca tgc cca ccg tgc cca gca cct gaa ctc ctg ggg     432
Asp Lys Thr His Thr Cys Pro Pro Cys Pro Ala Pro Glu Leu Leu Gly
    130                 135                 140 gga ccg tca gtc ttc ctc ttc ccc cca aaa ccc aag gac acc ctc atg     480
Gly Pro Ser Val Phe Leu Phe Pro Pro Lys Pro Lys Asp Thr Leu Met
145                 150                 155                 160 atc tcc cgg acc cct gag gtc aca tgc gtg gtg gtg gac gtg agc cac     528
Ile Ser Arg Thr Pro Glu Val Thr Cys Val Val Val Asp Val Ser His
                165                 170                 175 gaa gac cct gag gtc aag ttc aac tgg tac gtg gac ggc gtg gag gtg     576
Glu Asp Pro Glu Val Lys Phe Asn Trp Tyr Val Asp Gly Val Glu Val
            180                 185                 190 cat aat gcc aag aca aag ccg cgg gag gag cag tac aac agc acg tac     624
His Asn Ala Lys Thr Lys Pro Arg Glu Glu Gln Tyr Asn Ser Thr Tyr
        195                 200                 205 cgt gtg gtc agc gtc ctc acc gtc ctg cac cag gac tgg ctg aat ggc     672
Arg Val Val Ser Val Leu Thr Val Leu His Gln Asp Trp Leu Asn Gly
    210                 215                 220 aag gag tac aag tgc aag gtc tcc aac aaa gcc ctc cca gcc ccc atc     720
Lys Glu Tyr Lys Cys Lys Val Ser Asn Lys Ala Leu Pro Ala Pro Ile
225                 230                 235                 240 gag aaa acc atc tcc aaa gcc aaa ggg cag ccc cga gaa cca cag gtg     768
Glu Lys Thr Ile Ser Lys Ala Lys Gly Gln Pro Arg Glu Pro Gln Val
                245                 250                 255 tac acc ctg ccc cca tcc cgg gat aac ctg acc aag aac cag gtc agc     816
Tyr Thr Leu Pro Pro Ser Arg Asp Asn Leu Thr Lys Asn Gln Val Ser
            260                 265                 270 ctg acc tgc ctg gtc aaa ggc ttc tat ccc agc gac atc gcc gtg gag     864
Leu Thr Cys Leu Val Lys Gly Phe Tyr Pro Ser Asp Ile Ala Val Glu
        275                 280                 285 tgg gag agc aat ggg cag ccg gag aac aac acc aag acc acg cct ccc     912
Trp Glu Ser Asn Gly Gln Pro Glu Asn Asn Thr Lys Thr Thr Pro Pro
```

```
                  290                 295                 300
gtg ctg gac tcc gac ggc tcc ttc ttc ctc tat agc aag ctc acc gtg        960
Val Leu Asp Ser Asp Gly Ser Phe Phe Leu Tyr Ser Lys Leu Thr Val
305                 310                 315                 320 gac aag agc agg tgg cag cag ggg aac gtc ttc tca tgc tcc gtg atg       1008
Asp Lys Ser Arg Trp Gln Gln Gly Asn Val Phe Ser Cys Ser Val Met
                325                 330                 335 cat gag gct ctg cac aac cac tac acg cag aag agc ctc tcc ctg tcc       1056
His Glu Ala Leu His Asn His Tyr Thr Gln Lys Ser Leu Ser Leu Ser
            340                 345                 350 ccg ggt aaa     tga                                                    1068
Pro Gly Lys
        355

<210> SEQ ID NO 19
<211> LENGTH: 355
<212> TYPE: PRT
<213> ORGANISM: Homo sapiens

<400> SEQUENCE: 19

Gln Ile Thr Leu Lys Glu Ser Gly Pro Thr Leu Val Lys Pro Thr Gln
 1               5                   10                  15

Thr Leu Thr Leu Thr Cys Thr Phe Ser Gly Phe Ser Leu Ser Lys Ser
                20                  25                  30

Gly Val Gly Val Gly Trp Ile Arg Gln Pro Pro Gly Gln Ala Leu Glu
            35                  40                  45

Trp Leu Ala Leu Ile Phe Trp Asp Asp Asp Lys Arg Tyr Ser Pro Ser
        50                  55                  60

Leu Arg Thr Arg Leu Thr Ile Thr Lys Asp Thr Ser Lys Asn Gln Val
65                  70                  75                  80

Val Leu Thr Met Thr Asn Val Asp Pro Ala Asp Thr Ala Thr Tyr Tyr
                85                  90                  95

Cys Gly Tyr Ser Val Glu Gly Tyr Gly Gln Gly Tyr Arg Phe His Ser
            100                 105                 110

Trp Gly Gln Gly Thr Leu Val Thr Val Cys Ser Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Asn Leu Thr Lys Asn Gln Val Ser
            260                 265                 270

Leu Thr Cys Leu Val Lys Gly Phe Tyr Pro Ser Asp Ile Ala Val Glu
        275                 280                 285
```

|  |  |  |  |  |  |  |  |  |  |  |  |  |
|---|---|---|---|---|---|---|---|---|---|---|---|---|
| Trp | Glu | Ser | Asn | Gly | Gln | Pro | Glu | Asn | Asn | Thr | Lys | Thr | Thr | Pro | Pro |
|  |  | 290 |  |  |  | 295 |  |  |  | 300 |  |  |  |  |  |

| Val | Leu | Asp | Ser | Asp | Gly | Ser | Phe | Phe | Leu | Tyr | Ser | Lys | Leu | Thr | Val |
| 305 |  |  |  |  | 310 |  |  |  |  | 315 |  |  |  |  | 320 |

| Asp | Lys | Ser | Arg | Trp | Gln | Gln | Gly | Asn | Val | Phe | Ser | Cys | Ser | Val | Met |
|  |  |  |  | 325 |  |  |  |  | 330 |  |  |  |  | 335 |  |

| His | Glu | Ala | Leu | His | Asn | His | Tyr | Thr | Gln | Lys | Ser | Leu | Ser | Leu | Ser |
|  |  |  |  | 340 |  |  |  |  | 345 |  |  |  |  | 350 |  |

| Pro | Gly | Lys |
|  |  | 355 |

```
<210> SEQ ID NO 20
<211> LENGTH: 1068
<212> TYPE: DNA
<213> ORGANISM: Homo sapiens
<220> FEATURE:
<221> NAME/KEY: CDS
<222> LOCATION: (1)..(1065)
<223> OTHER INFORMATION: Ig-G3

<400> SEQUENCE: 20
```

| cag atc acc ttg aag gag tct ggt ccc acg ctg gtg aaa ccc aca cag | 48 |
|---|---|
| Gln Ile Thr Leu Lys Glu Ser Gly Pro Thr Leu Val Lys Pro Thr Gln |  |
|  1               5               10              15 |  |

| acc ctc acg ctg acc tgc acg ttc tct gga ttc tca ctc agc aaa agt | 96 |
| Thr Leu Thr Leu Thr Cys Thr Phe Ser Gly Phe Ser Leu Ser Lys Ser |  |
|          20              25              30 |  |

| gga gtg ggt gtg ggc tgg atc cgt cag ccc cca gga cag gcc ctg gag | 144 |
| Gly Val Gly Val Gly Trp Ile Arg Gln Pro Pro Gly Gln Ala Leu Glu |  |
|      35              40              45 |  |

| tgg ctt gca ctc att ttt tgg gat gat gat aag cgc tac agc cca tct | 192 |
| Trp Leu Ala Leu Ile Phe Trp Asp Asp Asp Lys Arg Tyr Ser Pro Ser |  |
|  50              55              60 |  |

| ctg agg acc aga ctc acc atc acc aag gac acc tcc aaa aac cag gtg | 240 |
| Leu Arg Thr Arg Leu Thr Ile Thr Lys Asp Thr Ser Lys Asn Gln Val |  |
| 65              70              75              80 |  |

| gtc ctt aca atg acc aac gtg gac cct gcg gac aca gcc aca tat tat | 288 |
| Val Leu Thr Met Thr Asn Val Asp Pro Ala Asp Thr Ala Thr Tyr Tyr |  |
|              85              90              95 |  |

| tgt gga tac agt gtt gaa gga tat ggc caa ggt tac cgc ttt cac tcc | 336 |
| Cys Gly Tyr Ser Val Glu Gly Tyr Gly Gln Gly Tyr Arg Phe His Ser |  |
|          100             105             110 |  |

| tgg ggc cag gga acc ctg gtc acc gtc tgc tca gag ccc aaa tct tgt | 384 |
| Trp Gly Gln Gly Thr Leu Val Thr Val Cys Ser Glu Pro Lys Ser Cys |  |
|      115             120             125 |  |

| gac aaa act cac aca tgc cca ccg tgc cca gca cct gaa ctc ctg ggg | 432 |
| Asp Lys Thr His Thr Cys Pro Pro Cys Pro Ala Pro Glu Leu Leu Gly |  |
| 130             135             140 |  |

| gga ccg tca gtc ttc ctc ttc ccc cca aaa ccc aag gac acc ctc atg | 480 |
| Gly Pro Ser Val Phe Leu Phe Pro Pro Lys Pro Lys Asp Thr Leu Met |  |
| 145             150             155             160 |  |

| atc tcc cgg acc cct gag gtc aca tgc gtg gtg gtg gac gtg agc cac | 528 |
| Ile Ser Arg Thr Pro Glu Val Thr Cys Val Val Val Asp Val Ser His |  |
|              165             170             175 |  |

| gaa gac cct gag gtc aag ttc aac tgg tac gtg gac ggc gtg gag gtg | 576 |
| Glu Asp Pro Glu Val Lys Phe Asn Trp Tyr Val Asp Gly Val Glu Val |  |
|          180             185             190 |  |

| cat aat gcc aag aca aag ccg cgg gag gag cag tac aac agc acg tac | 624 |
| His Asn Ala Lys Thr Lys Pro Arg Glu Glu Gln Tyr Asn Ser Thr Tyr |  |
|      195             200             205 |  |

-continued

| | | | |
|---|---|---|---|
| cgt gtg gtc agc gtc ctc acc gtc ctg cac cag gac tgg ctg aat ggc<br>Arg Val Val Ser Val Leu Thr Val Leu His Gln Asp Trp Leu Asn Gly<br>210                    215                    220 | | | 672 |
| aag gag tac aag tgc aag gtc tcc aac aaa gcc ctc cca gcc ccc atc<br>Lys Glu Tyr Lys Cys Lys Val Ser Asn Lys Ala Leu Pro Ala Pro Ile<br>225                    230                    235                    240 | | | 720 |
| gag aaa acc atc tcc aaa gcc aaa ggg cag ccc cga gaa cca cag gtg<br>Glu Lys Thr Ile Ser Lys Ala Lys Gly Gln Pro Arg Glu Pro Gln Val<br>                    245                    250                    255 | | | 768 |
| tac acc ctg ccc cca tcc cgg gat gag ctg acc aag aac cag gtc agc<br>Tyr Thr Leu Pro Pro Ser Arg Asp Glu Leu Thr Lys Asn Gln Val Ser<br>                260                    265                    270 | | | 816 |
| ctg acc tgc ctg gtc aaa ggc ttc tat ccc agc gac atc gcc gtg gag<br>Leu Thr Cys Leu Val Lys Gly Phe Tyr Pro Ser Asp Ile Ala Val Glu<br>              275                    280                    285 | | | 864 |
| tgg gag agc aat ggg cag ccg gag aac aac acc aag acc acg cct ccc<br>Trp Glu Ser Asn Gly Gln Pro Glu Asn Asn Thr Lys Thr Thr Pro Pro<br>290                    295                    300 | | | 912 |
| gtg ctg gac tcc gac ggc tcc ttc ttc ctc tat agc aag ctc acc gtg<br>Val Leu Asp Ser Asp Gly Ser Phe Phe Leu Tyr Ser Lys Leu Thr Val<br>305                    310                    315                    320 | | | 960 |
| gac aag agc agg tgg cag cag ggg aac gtc acc tca tgc tcc gtg atg<br>Asp Lys Ser Arg Trp Gln Gln Gly Asn Val Thr Ser Cys Ser Val Met<br>                325                    330                    335 | | | 1008 |
| cat gag gct ctg cac aac cac tac acg cag aag agc ctc tcc ctg tcc<br>His Glu Ala Leu His Asn His Tyr Thr Gln Lys Ser Leu Ser Leu Ser<br>                  340                    345                    350 | | | 1056 |
| ccg ggt aaa        tga<br>Pro Gly Lys<br>                355 | | | 1068 |

<210> SEQ ID NO 21
<211> LENGTH: 355
<212> TYPE: PRT
<213> ORGANISM: Homo sapiens

<400> SEQUENCE: 21

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Lys Ser
            20                  25                  30

Gly Val Gly Val Gly Trp Ile Arg Gln Pro Pro Gly Gln Ala Leu Glu
        35                  40                  45

Trp Leu Ala Leu Ile Phe Trp Asp Asp Asp Lys Arg Tyr Ser Pro Ser
    50                  55                  60

Leu Arg Thr Arg Leu Thr Ile Thr Lys Asp Thr Ser Lys Asn Gln Val
65                  70                  75                  80

Val Leu Thr Met Thr Asn Val Asp Pro Ala Asp Thr Ala Thr Tyr Tyr
                85                  90                  95

Cys Gly Tyr Ser Val Glu Gly Tyr Gly Gln Gly Tyr Arg Phe His Ser
            100                 105                 110

Trp Gly Gln Gly Thr Leu Val Thr Val Cys Ser Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

```
Ile Ser Arg Thr Pro Glu Val Thr Cys Val Val Asp Val Ser His
            165                 170                 175
Glu Asp Pro Glu Val Lys Phe Asn Trp Tyr Val Asp Gly Val Glu Val
            180                 185                 190
His Asn Ala Lys Thr Lys Pro Arg Glu Glu Gln Tyr Asn Ser Thr Tyr
            195                 200                 205
Arg Val Val Ser Val Leu Thr Val Leu His Gln Asp Trp Leu Asn Gly
            210                 215                 220
Lys Glu Tyr Lys Cys Lys Val Ser Asn Lys Ala Leu Pro Ala Pro Ile
225                 230                 235                 240
Glu Lys Thr Ile Ser Lys Ala Lys Gly Gln Pro Arg Glu Pro Gln Val
                245                 250                 255
Tyr Thr Leu Pro Pro Ser Arg Asp Glu Leu Thr Lys Asn Gln Val Ser
                260                 265                 270
Leu Thr Cys Leu Val Lys Gly Phe Tyr Pro Ser Asp Ile Ala Val Glu
            275                 280                 285
Trp Glu Ser Asn Gly Gln Pro Glu Asn Asn Thr Lys Thr Thr Pro Pro
            290                 295                 300
Val Leu Asp Ser Asp Gly Ser Phe Phe Leu Tyr Ser Lys Leu Thr Val
305                 310                 315                 320
Asp Lys Ser Arg Trp Gln Gln Gly Asn Val Thr Ser Cys Ser Val Met
                325                 330                 335
His Glu Ala Leu His Asn His Tyr Thr Gln Lys Ser Leu Ser Leu Ser
            340                 345                 350
Pro Gly Lys
        355

<210> SEQ ID NO 22
<211> LENGTH: 1068
<212> TYPE: DNA
<213> ORGANISM: Homo sapiens
<220> FEATURE:
<221> NAME/KEY: CDS
<222> LOCATION: (1)..(1065)
<223> OTHER INFORMATION: Ig-G4

<400> SEQUENCE: 22 cag atc acc ttg aag gag tct ggt ccc acg ctg gtg aaa ccc aca cag     48
Gln Ile Thr Leu Lys Glu Ser Gly Pro Thr Leu Val Lys Pro Thr Gln
 1               5                  10                  15 acc ctc acg ctg acc tgc acg ttc tct gga ttc tca ctc agc aaa agt     96
Thr Leu Thr Leu Thr Cys Thr Phe Ser Gly Phe Ser Leu Ser Lys Ser
             20                  25                  30 gga gtg ggt gtg ggc tgg atc cgt cag ccc cca gga cag gcc ctg gag    144
Gly Val Gly Val Gly Trp Ile Arg Gln Pro Pro Gly Gln Ala Leu Glu
         35                  40                  45 tgg ctt gca ctc att ttt tgg gat gat gat aag cgc tac agc cca tct    192
Trp Leu Ala Leu Ile Phe Trp Asp Asp Asp Lys Arg Tyr Ser Pro Ser
     50                  55                  60 ctg agg acc aga ctc acc atc acc aag gac acc tcc aaa aac cag gtg    240
Leu Arg Thr Arg Leu Thr Ile Thr Lys Asp Thr Ser Lys Asn Gln Val
 65                  70                  75                  80 gtc ctt aca atg acc aac gtg gac cct gcg gac aca gcc aca tat tat    288
Val Leu Thr Met Thr Asn Val Asp Pro Ala Asp Thr Ala Thr Tyr Tyr
                 85                  90                  95 tgt gga tac agt gtt gaa gga tat ggc caa ggt tac cgc ttt cac tcc    336
Cys Gly Tyr Ser Val Glu Gly Tyr Gly Gln Gly Tyr Arg Phe His Ser
            100                 105                 110
```

```
tgg ggc cag gga acc ctg gtc acc gtc tgc tca gag ccc aaa tct tgt         384
Trp Gly Gln Gly Thr Leu Val Thr Val Cys Ser Glu Pro Lys Ser Cys
            115                 120                 125 gac aaa act cac aca tgc cca ccg tgc cca gca cct gaa ctc ctg ggg         432
Asp Lys Thr His Thr Cys Pro Pro Cys Pro Ala Pro Glu Leu Leu Gly
        130                 135                 140 gga ccg tca gtc ttc ctc ttc ccc cca aaa ccc aag gac acc ctc aac         480
Gly Pro Ser Val Phe Leu Phe Pro Pro Lys Pro Lys Asp Thr Leu Asn
145                 150                 155                 160 atc tcc cgg acc cct gag gtc aca tgc gtg gtg gtg gac gtg agc cac         528
Ile Ser Arg Thr Pro Glu Val Thr Cys Val Val Val Asp Val Ser His
                165                 170                 175 gaa gac cct gag gtc aag ttc aac tgg tac gtg gac ggc gtg gag gtg         576
Glu Asp Pro Glu Val Lys Phe Asn Trp Tyr Val Asp Gly Val Glu Val
            180                 185                 190 cat aat gcc aag aca aag ccg cgg gag gag cag tac aac agc acg tac         624
His Asn Ala Lys Thr Lys Pro Arg Glu Glu Gln Tyr Asn Ser Thr Tyr
        195                 200                 205 cgt gtg gtc agc gtc ctc acc gtc ctg cac cag gac tgg ctg aat ggc         672
Arg Val Val Ser Val Leu Thr Val Leu His Gln Asp Trp Leu Asn Gly
210                 215                 220 aag gag tac aag tgc aag gtc tcc aac aaa gcc ctc cca gcc ccc atc         720
Lys Glu Tyr Lys Cys Lys Val Ser Asn Lys Ala Leu Pro Ala Pro Ile
225                 230                 235                 240 gag aaa acc atc tcc aaa gcc aaa ggg cag ccc cga gaa cca cag gtg         768
Glu Lys Thr Ile Ser Lys Ala Lys Gly Gln Pro Arg Glu Pro Gln Val
                245                 250                 255 tac acc ctg ccc cca tcc cgg gat aac ctg acc aag aac cag gtc agc         816
Tyr Thr Leu Pro Pro Ser Arg Asp Asn Leu Thr Lys Asn Gln Val Ser
            260                 265                 270 ctg acc tgc ctg gtc aaa ggc ttc tat ccc agc gac atc gcc gtg gag         864
Leu Thr Cys Leu Val Lys Gly Phe Tyr Pro Ser Asp Ile Ala Val Glu
        275                 280                 285 tgg gag agc aat ggg cag ccg gag aac aac acc aag acc acg cct ccc         912
Trp Glu Ser Asn Gly Gln Pro Glu Asn Asn Thr Lys Thr Thr Pro Pro
    290                 295                 300 gtg ctg gac tcc gac ggc tcc ttc ttc ctc tat agc aag ctc acc gtg         960
Val Leu Asp Ser Asp Gly Ser Phe Phe Leu Tyr Ser Lys Leu Thr Val
305                 310                 315                 320 gac aag agc agg tgg cag cag ggg aac gtc ttc tca tgc tcc gtg atg        1008
Asp Lys Ser Arg Trp Gln Gln Gly Asn Val Phe Ser Cys Ser Val Met
                325                 330                 335 cat gag gct ctg cac aac cac tac acg cag aag agc ctc tcc ctg tcc        1056
His Glu Ala Leu His Asn His Tyr Thr Gln Lys Ser Leu Ser Leu Ser
            340                 345                 350 ccg ggt aaa     tga                                                    1068
Pro Gly Lys
        355

<210> SEQ ID NO 23
<211> LENGTH: 355
<212> TYPE: PRT
<213> ORGANISM: Homo sapiens

<400> SEQUENCE: 23

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Lys Ser
            20                  25                  30

Gly Val Gly Val Gly Trp Ile Arg Gln Pro Pro Gly Gln Ala Leu Glu
```

```
                35                  40                  45
Trp Leu Ala Leu Ile Phe Trp Asp Asp Lys Arg Tyr Ser Pro Ser
     50                  55                  60

Leu Arg Thr Arg Leu Thr Ile Thr Lys Asp Thr Ser Lys Asn Gln Val
 65                  70                  75                  80

Val Leu Thr Met Thr Asn Val Asp Pro Ala Asp Thr Ala Thr Tyr Tyr
                 85                  90                  95

Cys Gly Tyr Ser Val Glu Gly Tyr Gly Gln Gly Tyr Arg Phe His Ser
            100                 105                 110

Trp Gly Gln Gly Thr Leu Val Thr Val Cys Ser Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Asn
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Asn Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Thr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Lys
        355

<210> SEQ ID NO 24
<211> LENGTH: 1068
<212> TYPE: DNA
<213> ORGANISM: Homo sapiens
<220> FEATURE:
<221> NAME/KEY: CDS
<222> LOCATION: (1)..(1065)
<223> OTHER INFORMATION: Ig-G5

<400> SEQUENCE: 24 cag atc acc ttg aag gag tct ggt ccc acg ctg gtg aaa ccc aca cag      48
Gln Ile Thr Leu Lys Glu Ser Gly Pro Thr Leu Val Lys Pro Thr Gln
  1               5                  10                  15 acc ctc acg ctg acc tgc acg ttc tct gga ttc tca ctc agc aaa agt      96
```

```
                Thr Leu Thr Leu Thr Cys Thr Phe Ser Gly Phe Ser Leu Ser Lys Ser
                                 20                  25                  30 gga gtg ggt gtg ggc tgg atc cgt cag ccc cca gga cag gcc ctg gag             144
Gly Val Gly Val Gly Trp Ile Arg Gln Pro Pro Gly Gln Ala Leu Glu
                 35                  40                  45 tgg ctt gca ctc att ttt tgg gat gat gat aag cgc tac agc cca tct             192
Trp Leu Ala Leu Ile Phe Trp Asp Asp Asp Lys Arg Tyr Ser Pro Ser
     50                  55                  60 ctg agg acc aga ctc acc atc acc aag gac acc tcc aaa aac cag gtg             240
Leu Arg Thr Arg Leu Thr Ile Thr Lys Asp Thr Ser Lys Asn Gln Val
 65                  70                  75                  80 gtc ctt aca atg acc aac gtg gac cct gcg gac aca gcc aca tat tat             288
Val Leu Thr Met Thr Asn Val Asp Pro Ala Asp Thr Ala Thr Tyr Tyr
                 85                  90                  95 tgt gga tac agt gtt gaa gga tat ggc caa ggt tac cgc ttt cac tcc             336
Cys Gly Tyr Ser Val Glu Gly Tyr Gly Gln Gly Tyr Arg Phe His Ser
                100                 105                 110 tgg ggc cag gga acc ctg gtc acc gtc tgc tca gag ccc aaa tct tgt             384
Trp Gly Gln Gly Thr Leu Val Thr Val Cys Ser Glu Pro Lys Ser Cys
            115                 120                 125 gac aaa act cac aca tgc cca ccg tgc cca gca cct gaa ctc ctg ggg             432
Asp Lys Thr His Thr Cys Pro Pro Cys Pro Ala Pro Glu Leu Leu Gly
        130                 135                 140 gga ccg tca gtc ttc ctc ttc ccc cca aaa ccc aag gac acc ctc aac             480
Gly Pro Ser Val Phe Leu Phe Pro Pro Lys Pro Lys Asp Thr Leu Asn
145                 150                 155                 160 atc tcc cgg acc cct gag gtc aca tgc gtg gtg gtg gac gtg agc cac             528
Ile Ser Arg Thr Pro Glu Val Thr Cys Val Val Val Asp Val Ser His
                165                 170                 175 gaa gac cct gag gtc aag ttc aac tgg tac gtg gac ggc gtg gag gtg             576
Glu Asp Pro Glu Val Lys Phe Asn Trp Tyr Val Asp Gly Val Glu Val
                180                 185                 190 cat aat gcc aag aca aag ccg cgg gag gag cag tac aac agc acg tac             624
His Asn Ala Lys Thr Lys Pro Arg Glu Glu Gln Tyr Asn Ser Thr Tyr
            195                 200                 205 cgt gtg gtc agc gtc ctc acc gtc ctg cac cag gac tgg ctg aat ggc             672
Arg Val Val Ser Val Leu Thr Val Leu His Gln Asp Trp Leu Asn Gly
        210                 215                 220 aag gag tac aag tgc aag gtc tcc aac aaa gcc ctc cca gcc ccc atc             720
Lys Glu Tyr Lys Cys Lys Val Ser Asn Lys Ala Leu Pro Ala Pro Ile
225                 230                 235                 240 gag aaa acc atc tcc aaa gcc aaa ggg cag ccc cga gaa cca cag gtg             768
Glu Lys Thr Ile Ser Lys Ala Lys Gly Gln Pro Arg Glu Pro Gln Val
                245                 250                 255 tac acc ctg ccc cca tcc cgg gat aac ctg acc aag aac cag gtc agc             816
Tyr Thr Leu Pro Pro Ser Arg Asp Asn Leu Thr Lys Asn Gln Val Ser
                260                 265                 270 ctg acc tgc ctg gtc aaa ggc ttc tat ccc agc gac atc gcc gtg gag             864
Leu Thr Cys Leu Val Lys Gly Phe Tyr Pro Ser Asp Ile Ala Val Glu
            275                 280                 285 tgg gag agc aat ggg cag ccg gag aac aac acc aag acc acg cct ccc             912
Trp Glu Ser Asn Gly Gln Pro Glu Asn Asn Thr Lys Thr Thr Pro Pro
        290                 295                 300 gtg ctg gac tcc gac ggc tcc ttc ttc ctc tat agc aag ctc acc gtg             960
Val Leu Asp Ser Asp Gly Ser Phe Phe Leu Tyr Ser Lys Leu Thr Val
305                 310                 315                 320 gac aag agc agg tgg cag cag ggg aac gtc acc tca tgc tcc gtg atg             1008
Asp Lys Ser Arg Trp Gln Gln Gly Asn Val Thr Ser Cys Ser Val Met
                325                 330                 335
```

-continued

```
cat gag gct ctg cac aac cac tac acg cag aag agc ctc tcc ctg tcc      1056
His Glu Ala Leu His Asn His Tyr Thr Gln Lys Ser Leu Ser Leu Ser
            340                 345                 350 ccg ggt aaa     tga                                                    1068
Pro Gly Lys
        355

<210> SEQ ID NO 25
<211> LENGTH: 355
<212> TYPE: PRT
<213> ORGANISM: Homo sapiens

<400> SEQUENCE: 25

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Lys Ser
             20                  25                  30

Gly Val Gly Val Gly Trp Ile Arg Gln Pro Pro Gly Gln Ala Leu Glu
         35                  40                  45

Trp Leu Ala Leu Ile Phe Trp Asp Asp Lys Arg Tyr Ser Pro Ser
     50                  55                  60

Leu Arg Thr Arg Leu Thr Ile Thr Lys Asp Thr Ser Lys Asn Gln Val
 65                  70                  75                  80

Val Leu Thr Met Thr Asn Val Asp Pro Ala Asp Thr Ala Thr Tyr Tyr
                 85                  90                  95

Cys Gly Tyr Ser Val Glu Gly Tyr Gly Gln Gly Tyr Arg Phe His Ser
            100                 105                 110

Trp Gly Gln Gly Thr Leu Val Thr Val Cys Ser Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Asn
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Asn Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Thr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Thr Ser Cys Ser Val Met
                325                 330                 335
```

```
                    His Glu Ala Leu His Asn His Tyr Thr Gln Lys Ser Leu Ser Leu Ser
                                340                 345                 350

Pro Gly Lys
                            355

<210> SEQ ID NO 26
<211> LENGTH: 1068
<212> TYPE: DNA
<213> ORGANISM: Homo sapiens
<220> FEATURE:
<221> NAME/KEY: CDS
<222> LOCATION: (1)..(1065)
<223> OTHER INFORMATION: Ig-G6

<400> SEQUENCE: 26 cag atc acc ttg aag gag tct ggt ccc acg ctg gtg aaa ccc aca cag     48
Gln Ile Thr Leu Lys Glu Ser Gly Pro Thr Leu Val Lys Pro Thr Gln
  1               5                  10                  15 acc ctc acg ctg acc tgc acg ttc tct gga ttc tca ctc agc aaa agt     96
Thr Leu Thr Leu Thr Cys Thr Phe Ser Gly Phe Ser Leu Ser Lys Ser
             20                  25                  30 gga gtg ggt gtg ggc tgg atc cgt cag ccc cca gga cag gcc ctg gag    144
Gly Val Gly Val Gly Trp Ile Arg Gln Pro Pro Gly Gln Ala Leu Glu
         35                  40                  45 tgg ctt gca ctc att ttt tgg gat gat gat aag cgc tac agc cca tct    192
Trp Leu Ala Leu Ile Phe Trp Asp Asp Asp Lys Arg Tyr Ser Pro Ser
     50                  55                  60 ctg agg acc aga ctc acc atc acc aag gac acc tcc aaa aac cag gtg    240
Leu Arg Thr Arg Leu Thr Ile Thr Lys Asp Thr Ser Lys Asn Gln Val
 65                  70                  75                  80 gtc ctt aca atg acc aac gtg gac cct gcg gac aca gcc aca tat tat    288
Val Leu Thr Met Thr Asn Val Asp Pro Ala Asp Thr Ala Thr Tyr Tyr
                 85                  90                  95 tgt gga tac agt gtt gaa gga tat ggc caa ggt tac cgc ttt cac tcc    336
Cys Gly Tyr Ser Val Glu Gly Tyr Gly Gln Gly Tyr Arg Phe His Ser
            100                 105                 110 tgg ggc cag gga acc ctg gtc acc gtc tgc tca gag ccc aaa tct tgt    384
Trp Gly Gln Gly Thr Leu Val Thr Val Cys Ser Glu Pro Lys Ser Cys
        115                 120                 125 gac aaa act cac aca tgc cca ccg tgc cca gca cct gaa ctc ctg ggg    432
Asp Lys Thr His Thr Cys Pro Pro Cys Pro Ala Pro Glu Leu Leu Gly
    130                 135                 140 gga ccg tca gtc ttc ctc ttc ccc cca aaa ccc aag gac acc ctc aac    480
Gly Pro Ser Val Phe Leu Phe Pro Pro Lys Pro Lys Asp Thr Leu Asn
145                 150                 155                 160 atc tcc cgg acc cct gag gtc aca tgc gtg gtg gtg gac gtg agc cac    528
Ile Ser Arg Thr Pro Glu Val Thr Cys Val Val Val Asp Val Ser His
                165                 170                 175 gaa gac cct gag gtc aag ttc aac tgg tac gtg gac ggc gtg gag gtg    576
Glu Asp Pro Glu Val Lys Phe Asn Trp Tyr Val Asp Gly Val Glu Val
            180                 185                 190 cat aat aac aag aca aag ccg cgg gag gag cag tac aac agc acg tac    624
His Asn Asn Lys Thr Lys Pro Arg Glu Glu Gln Tyr Asn Ser Thr Tyr
        195                 200                 205 cgt gtg gtc agc gtc ctc acc gtc ctg cac cag gac tgg ctg aat ggc    672
Arg Val Val Ser Val Leu Thr Val Leu His Gln Asp Trp Leu Asn Gly
    210                 215                 220 aag gag tac aag tgc aag gtc tcc aac aaa gcc ctc cca gcc ccc atc    720
Lys Glu Tyr Lys Cys Lys Val Ser Asn Lys Ala Leu Pro Ala Pro Ile
225                 230                 235                 240 gag aaa acc atc tcc aaa gcc aaa ggg cag ccc cga gaa cca cag gtg    768
Glu Lys Thr Ile Ser Lys Ala Lys Gly Gln Pro Arg Glu Pro Gln Val
```

```
Glu Lys Thr Ile Ser Lys Ala Lys Gly Gln Pro Arg Glu Pro Gln Val
                245                 250                 255 tac acc ctg ccc cca tcc cgg gat aac ctg acc aag aac cag gtc agc       816
Tyr Thr Leu Pro Pro Ser Arg Asp Asn Leu Thr Lys Asn Gln Val Ser
            260                 265                 270 ctg acc tgc ctg gtc aaa ggc ttc tat ccc agc gac atc gcc gtg gag       864
Leu Thr Cys Leu Val Lys Gly Phe Tyr Pro Ser Asp Ile Ala Val Glu
        275                 280                 285 tgg gag agc aat ggg cag ccg gag aac aac acc aag acc acg cct ccc       912
Trp Glu Ser Asn Gly Gln Pro Glu Asn Asn Thr Lys Thr Thr Pro Pro
    290                 295                 300 gtg ctg gac tcc gac ggc tcc ttc ttc ctc tat agc aag ctc acc gtg       960
Val Leu Asp Ser Asp Gly Ser Phe Phe Leu Tyr Ser Lys Leu Thr Val
305                 310                 315                 320 gac aag agc agg tgg cag cag ggg aac gtc acc tca tgc tcc gtg atg      1008
Asp Lys Ser Arg Trp Gln Gln Gly Asn Val Thr Ser Cys Ser Val Met
                325                 330                 335 cat gag gct ctg cac aac cac tac acg cag aag agc ctc tcc ctg tcc      1056
His Glu Ala Leu His Asn His Tyr Thr Gln Lys Ser Leu Ser Leu Ser
            340                 345                 350 ccg ggt aaa      tga                                                 1068
Pro Gly Lys
        355

<210> SEQ ID NO 27
<211> LENGTH: 355
<212> TYPE: PRT
<213> ORGANISM: Homo sapiens

<400> SEQUENCE: 27

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Lys Ser
            20                  25                  30

Gly Val Gly Val Gly Trp Ile Arg Gln Pro Pro Gly Gln Ala Leu Glu
        35                  40                  45

Trp Leu Ala Leu Ile Phe Trp Asp Asp Asp Lys Arg Tyr Ser Pro Ser
    50                  55                  60

Leu Arg Thr Arg Leu Thr Ile Thr Lys Asp Thr Ser Lys Asn Gln Val
65                  70                  75                  80

Val Leu Thr Met Thr Asn Val Asp Pro Ala Asp Thr Ala Thr Tyr Tyr
                85                  90                  95

Cys Gly Tyr Ser Val Glu Gly Tyr Gly Gln Gly Tyr Arg Phe His Ser
            100                 105                 110

Trp Gly Gln Gly Thr Leu Val Thr Val Cys Ser Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Asn
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Asn Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
```

```
                    210                 215                 220
Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Asn Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Thr Lys Thr Thr Pro Pro
290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Thr Ser Cys Ser Val Met
                325                 330                 335

His Glu Ala Leu His Asn His Tyr Thr Gln Lys Ser Leu Ser Leu Ser
            340                 345                 350

Pro Gly Lys
        355

<210> SEQ ID NO 28
<211> LENGTH: 1068
<212> TYPE: DNA
<213> ORGANISM: Homo sapiens
<220> FEATURE:
<221> NAME/KEY: CDS
<222> LOCATION: (1)..(1065)
<223> OTHER INFORMATION: Ig-G7

<400> SEQUENCE: 28 cag atc acc ttg aag gag tct ggt ccc acg ctg gtg aaa ccc aca cag    48
Gln Ile Thr Leu Lys Glu Ser Gly Pro Thr Leu Val Lys Pro Thr Gln
  1               5                  10                  15 acc ctc acg ctg acc tgc acg ttc tct gga ttc tca ctc agc aaa agt    96
Thr Leu Thr Leu Thr Cys Thr Phe Ser Gly Phe Ser Leu Ser Lys Ser
             20                  25                  30 gga gtg ggt gtg ggc tgg atc cgt cag ccc cca gga cag gcc ctg gag   144
Gly Val Gly Val Gly Trp Ile Arg Gln Pro Pro Gly Gln Ala Leu Glu
         35                  40                  45 tgg ctt gca ctc att ttt tgg gat gat gat aag cgc tac agc cca tct   192
Trp Leu Ala Leu Ile Phe Trp Asp Asp Asp Lys Arg Tyr Ser Pro Ser
     50                  55                  60 ctg agg acc aga ctc acc atc acc aag gac acc tcc aaa aac cag gtg   240
Leu Arg Thr Arg Leu Thr Ile Thr Lys Asp Thr Ser Lys Asn Gln Val
 65                  70                  75                  80 gtc ctt aca atg acc aac gtg gac cct gcg gac aca gcc aca tat tat   288
Val Leu Thr Met Thr Asn Val Asp Pro Ala Asp Thr Ala Thr Tyr Tyr
                 85                  90                  95 tgt gga tac agt gtt gaa gga tat ggc caa ggt tac cgc ttt cac tcc   336
Cys Gly Tyr Ser Val Glu Gly Tyr Gly Gln Gly Tyr Arg Phe His Ser
            100                 105                 110 tgg ggc cag gga acc ctg gtc acc gtc tgc tca gag ccc aaa tct tgt   384
Trp Gly Gln Gly Thr Leu Val Thr Val Cys Ser Glu Pro Lys Ser Cys
        115                 120                 125 gac aaa act cac aca tgc cca ccg tgc cca gca cct gaa ctc ctg ggg   432
Asp Lys Thr His Thr Cys Pro Pro Cys Pro Ala Pro Glu Leu Leu Gly
    130                 135                 140 gga ccg tca gtc ttc ctc ttc ccc cca aaa ccc aag gac acc ctc aac   480
Gly Pro Ser Val Phe Leu Phe Pro Pro Lys Pro Lys Asp Thr Leu Asn
145                 150                 155                 160
```

| | | | | |
|---|---|---|---|---|
| atc tcc cgg acc cct gag gtc aca tgc gtg gtg gtg gac gtg agc cac<br>Ile Ser Arg Thr Pro Glu Val Thr Cys Val Val Val Asp Val Ser His<br>              165                    170                    175 | 528 |

| | |
|---|---|
| atc tcc cgg acc cct gag gtc aca tgc gtg gtg gtg gac gtg agc cac<br>Ile Ser Arg Thr Pro Glu Val Thr Cys Val Val Val Asp Val Ser His<br>165 170 175 | 528 |
| gaa gac cct gag gtc aag ttc aac tgg tac gtg gac ggc gtg gag gtg<br>Glu Asp Pro Glu Val Lys Phe Asn Trp Tyr Val Asp Gly Val Glu Val<br>180 185 190 | 576 |
| cat aat aac aag aca aag ccg cgg gag gag cag tac aac agc acg tac<br>His Asn Asn Lys Thr Lys Pro Arg Glu Glu Gln Tyr Asn Ser Thr Tyr<br>195 200 205 | 624 |
| cgt gtg gtc agc gtc ctc acc gtc ctg cac cag gac tgg ctg aat ggc<br>Arg Val Val Ser Val Leu Thr Val Leu His Gln Asp Trp Leu Asn Gly<br>210 215 220 | 672 |
| aag gag tac aag tgc aag gtc tcc aac aaa gcc ctc cca gcc ccc atc<br>Lys Glu Tyr Lys Cys Lys Val Ser Asn Lys Ala Leu Pro Ala Pro Ile<br>225 230 235 240 | 720 |
| gag aaa aac atc tcc aaa gcc aaa ggg cag ccc cga gaa cca cag gtg<br>Glu Lys Asn Ile Ser Lys Ala Lys Gly Gln Pro Arg Glu Pro Gln Val<br>245 250 255 | 768 |
| tac acc ctg ccc cca tcc cgg gat aac ctg acc aag aac cag gtc agc<br>Tyr Thr Leu Pro Pro Ser Arg Asp Asn Leu Thr Lys Asn Gln Val Ser<br>260 265 270 | 816 |
| ctg acc tgc ctg gtc aaa ggc ttc tat ccc agc gac atc gcc gtg gag<br>Leu Thr Cys Leu Val Lys Gly Phe Tyr Pro Ser Asp Ile Ala Val Glu<br>275 280 285 | 864 |
| tgg gag agc aat ggg cag ccg gag aac aac acc aag acc acg cct ccc<br>Trp Glu Ser Asn Gly Gln Pro Glu Asn Asn Thr Lys Thr Thr Pro Pro<br>290 295 300 | 912 |
| gtg ctg gac tcc gac ggc tcc ttc ttc ctc tat agc aag ctc acc gtg<br>Val Leu Asp Ser Asp Gly Ser Phe Phe Leu Tyr Ser Lys Leu Thr Val<br>305 310 315 320 | 960 |
| gac aag agc agg tgg cag cag ggg aac gtc acc tca tgc tcc gtg atg<br>Asp Lys Ser Arg Trp Gln Gln Gly Asn Val Thr Ser Cys Ser Val Met<br>325 330 335 | 1008 |
| cat gag gct ctg cac aac cac tac acg cag aag agc ctc tcc ctg tcc<br>His Glu Ala Leu His Asn His Tyr Thr Gln Lys Ser Leu Ser Leu Ser<br>340 345 350 | 1056 |
| ccg ggt aaa     tga<br>Pro Gly Lys<br>355 | 1068 |

<210> SEQ ID NO 29
<211> LENGTH: 355
<212> TYPE: PRT
<213> ORGANISM: Homo sapiens

<400> SEQUENCE: 29

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Lys Ser
            20                  25                  30

Gly Val Gly Val Gly Trp Ile Arg Gln Pro Pro Gly Gln Ala Leu Glu
        35                  40                  45

Trp Leu Ala Leu Ile Phe Trp Asp Asp Asp Lys Arg Tyr Ser Pro Ser
    50                  55                  60

Leu Arg Thr Arg Leu Thr Ile Thr Lys Asp Thr Ser Lys Asn Gln Val
65                  70                  75                  80

Val Leu Thr Met Thr Asn Val Asp Pro Ala Asp Thr Ala Thr Tyr Tyr
                85                  90                  95

Cys Gly Tyr Ser Val Glu Gly Tyr Gly Gln Gly Tyr Arg Phe His Ser
            100                 105                 110

Trp Gly Gln Gly Thr Leu Val Thr Val Cys Ser Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Asn
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Asn Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Asn Ile Ser Lys Ala Lys Gly Gln Pro Arg Glu Pro Gln Val
                245                 250                 255

Tyr Thr Leu Pro Pro Ser Arg Asp Asn Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Thr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Thr Ser Cys Ser Val Met
                325                 330                 335

His Glu Ala Leu His Asn His Tyr Thr Gln Lys Ser Leu Ser Leu Ser
            340                 345                 350

Pro Gly Lys
        355

<210> SEQ ID NO 30
<211> LENGTH: 1068
<212> TYPE: DNA
<213> ORGANISM: Homo sapiens
<220> FEATURE:
<221> NAME/KEY: CDS
<222> LOCATION: (1)..(1065)
<223> OTHER INFORMATION: Ig-G8

<400> SEQUENCE: 30

```
cag atc acc ttg aag gag tct ggt ccc acg ctg gtg aaa ccc aca cag      48
Gln Ile Thr Leu Lys Glu Ser Gly Pro Thr Leu Val Lys Pro Thr Gln
  1               5                  10                  15 acc ctc acg ctg acc tgc acg ttc tct gga ttc tca ctc agc aaa agt      96
Thr Leu Thr Leu Thr Cys Thr Phe Ser Gly Phe Ser Leu Ser Lys Ser
             20                  25                  30 gga gtg ggt gtg ggc tgg atc cgt cag ccc cca gga cag gcc ctg gag     144
Gly Val Gly Val Gly Trp Ile Arg Gln Pro Pro Gly Gln Ala Leu Glu
         35                  40                  45 tgg ctt gca ctc att ttt tgg gat gat gat aag cgc tac agc cca tct     192
Trp Leu Ala Leu Ile Phe Trp Asp Asp Asp Lys Arg Tyr Ser Pro Ser
     50                  55                  60
```

```
ctg agg acc aga ctc acc atc acc aag gac acc tcc aaa aac cag gtg      240
Leu Arg Thr Arg Leu Thr Ile Thr Lys Asp Thr Ser Lys Asn Gln Val
 65                  70                  75                  80 gtc ctt aca atg acc aac gtg gac cct gcg gac aca gcc aca tat tat      288
Val Leu Thr Met Thr Asn Val Asp Pro Ala Asp Thr Ala Thr Tyr Tyr
                 85                  90                  95 tgt gga tac agt gtt gaa gga tat ggc caa ggt tac cgc ttt cac tcc      336
Cys Gly Tyr Ser Val Glu Gly Tyr Gly Gln Gly Tyr Arg Phe His Ser
            100                 105                 110 tgg ggc cag gga acc ctg gtc acc gtc tgc tca gag ccc aaa tct tgt      384
Trp Gly Gln Gly Thr Leu Val Thr Val Cys Ser Glu Pro Lys Ser Cys
        115                 120                 125 gac aaa act cac aca tgc cca ccg tgc cca gca cct gaa ctc ctg ggg      432
Asp Lys Thr His Thr Cys Pro Pro Cys Pro Ala Pro Glu Leu Leu Gly
130                 135                 140 gga ccg tca gtc ttc ctc ttc ccc cca aaa ccc aag gac acc ctc aac      480
Gly Pro Ser Val Phe Leu Phe Pro Pro Lys Pro Lys Asp Thr Leu Asn
145                 150                 155                 160 atc tcc cgg acc cct gag gtc aca tgc gtg gtg gtg gac gtg agc cac      528
Ile Ser Arg Thr Pro Glu Val Thr Cys Val Val Val Asp Val Ser His
                165                 170                 175 gaa gac cct gag gtc aag ttc aac tgg tac gtg gac ggc gtg gag gtg      576
Glu Asp Pro Glu Val Lys Phe Asn Trp Tyr Val Asp Gly Val Glu Val
            180                 185                 190 cat aat aac aag aca aag ccg cgg gag gag cag tac aac agc acg tac      624
His Asn Asn Lys Thr Lys Pro Arg Glu Glu Gln Tyr Asn Ser Thr Tyr
        195                 200                 205 cgt gtg gtc agc gtc ctc acc gtc ctg cac cag gac tgg ctg aat ggc      672
Arg Val Val Ser Val Leu Thr Val Leu His Gln Asp Trp Leu Asn Gly
210                 215                 220 aag gag tac aag tgc aag gtc tcc aac aaa gcc ctc cca gcc ccc atc      720
Lys Glu Tyr Lys Cys Lys Val Ser Asn Lys Ala Leu Pro Ala Pro Ile
225                 230                 235                 240 gag aaa aac atc tcc aaa gcc aaa ggg cag ccc cga gaa cca cag gtg      768
Glu Lys Asn Ile Ser Lys Ala Lys Gly Gln Pro Arg Glu Pro Gln Val
                245                 250                 255 tac acc ctg ccc cca tcc cgg gat aac ctg acc aag aac cag gtc agc      816
Tyr Thr Leu Pro Pro Ser Arg Asp Asn Leu Thr Lys Asn Gln Val Ser
            260                 265                 270 ctg acc tgc ctg gtc aaa ggc ttc tat ccc agc gac atc gcc gtg gag      864
Leu Thr Cys Leu Val Lys Gly Phe Tyr Pro Ser Asp Ile Ala Val Glu
        275                 280                 285 tgg gag agc aat ggg cag ccg gag aac aac acc aag acc acg cct ccc      912
Trp Glu Ser Asn Gly Gln Pro Glu Asn Asn Thr Lys Thr Thr Pro Pro
290                 295                 300 gtg ctg gac tcc gac ggc tcc ttc ttc ctc tat agc aag ctc acc gtg      960
Val Leu Asp Ser Asp Gly Ser Phe Phe Leu Tyr Ser Lys Leu Thr Val
305                 310                 315                 320 gac aag agc agg tgg cag cag ggg aac gtc acc tca tgc tcc gtg atg     1008
Asp Lys Ser Arg Trp Gln Gln Gly Asn Val Thr Ser Cys Ser Val Met
                325                 330                 335 cat gag gct ctg cac aac cac tac acg aac aag agc ctc tcc ctg tcc     1056
His Glu Ala Leu His Asn His Tyr Thr Asn Lys Ser Leu Ser Leu Ser
            340                 345                 350 ccg ggt aaa     tga                                                 1068
Pro Gly Lys
        355
```

<210> SEQ ID NO 31

<211> LENGTH: 355
<212> TYPE: PRT
<213> ORGANISM: Homo sapiens

<400> SEQUENCE: 31

```
Gln Ile Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Lys Ser
             20                  25                  30

Gly Val Gly Val Gly Trp Ile Arg Gln Pro Pro Gly Gln Ala Leu Glu
         35                  40                  45

Trp Leu Ala Leu Ile Phe Trp Asp Asp Asp Lys Arg Tyr Ser Pro Ser
 50                  55                  60

Leu Arg Thr Arg Leu Thr Ile Thr Lys Asp Thr Ser Lys Asn Gln Val
 65                  70                  75                  80

Val Leu Thr Met Thr Asn Val Asp Pro Ala Asp Thr Ala Thr Tyr Tyr
                 85                  90                  95

Cys Gly Tyr Ser Val Glu Gly Tyr Gly Gln Gly Tyr Arg Phe His Ser
            100                 105                 110

Trp Gly Gln Gly Thr Leu Val Thr Val Cys Ser Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Asn
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Asn Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Asn Ile Ser Lys Ala Lys Gly Gln Pro Arg Glu Pro Gln Val
                245                 250                 255

Tyr Thr Leu Pro Pro Ser Arg Asp Asn Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Thr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Thr Ser Cys Ser Val Met
                325                 330                 335

His Glu Ala Leu His Asn His Tyr Thr Asn Lys Ser Leu Ser Leu Ser
            340                 345                 350

Pro Gly Lys
        355
```